(12) United States Patent
Sato

(10) Patent No.: US 8,606,597 B2
(45) Date of Patent: Dec. 10, 2013

(54) ENDOSCOPE INSPECTION REPORT CREATING APPARATUS, CREATING METHOD OF ENDOSCOPE INSPECTION REPORT AND STORAGE MEDIUM

(75) Inventor: Saichi Sato, Sagamihara (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/402,325

(22) Filed: Feb. 22, 2012

(65) Prior Publication Data

US 2012/0221569 A1 Aug. 30, 2012

Related U.S. Application Data

(60) Provisional application No. 61/446,181, filed on Feb. 24, 2011.

(51) Int. Cl.
*G06F 17/27* (2006.01)

(52) U.S. Cl.
USPC .................................. 705/2; 396/17; 707/736

(58) Field of Classification Search
None
See application file for complete search history.

(56) References Cited

U.S. PATENT DOCUMENTS

| | | | |
|---|---|---|---|
| 2006/0149156 A1* | 7/2006 | Cochran et al. | 600/509 |
| 2010/0036676 A1* | 2/2010 | Safdi et al. | 705/2 |
| 2010/0114597 A1* | 5/2010 | Shreiber et al. | 705/2 |

FOREIGN PATENT DOCUMENTS

| | | |
|---|---|---|
| JP | 2003-009057 A | 1/2003 |
| JP | 2006-276991 A | 10/2006 |

* cited by examiner

*Primary Examiner* — Neveen Abel Jalil
*Assistant Examiner* — Michael K Tamaru
(74) *Attorney, Agent, or Firm* — Holtz, Holtz, Goodman & Chick, PC

(57) ABSTRACT

An endoscope inspection report creating apparatus has a file name reading section that reads file names of a plurality of endoscopic images, a file name of each of the endoscopic images including inspection result information separated with use of a predetermined symbol or character, and a report creating section that creates a predetermined report by writing the inspection result information which is included in each of the file names read by the file name reading section in each predetermined position in the predetermined report by associating the inspection result information with the endoscopic image of each of the read file names.

25 Claims, 13 Drawing Sheets

ENGINE1_SN001_HPC_STAGE1_ZONE1_1_A_001.jpg

- 81: ENGINE1_SN001
- 82: HPC_STAGE1_ZONE1_1
- 83: A
- 84: 001

| Area | Block Location | Reason for Inspection | Outcome | Picture |
|---|---|---|---|---|
| HPC | STAGE1_ZONE1 | Cracks | Accept |  |
| | | | Accept |  |
| HPC | STAGE1_ZONE1 | Surface Defects | Re-Inspect Some Defects |  |
| HPC | STAGE1_ZONE2 | Cracks | Reject Cracks |  |

| A | Accept |
|---|---|
| B | Reject |
| C | Repair |
| C | Re-Inspect |

FIG.16

| Area | Block Location | Reason for Inspection | Outcome | Picture |
|---|---|---|---|---|
| | | | . | . |
| HPC | STAGE4_ZONE3 | Cracks | Accept | NO PHOTO |
| HPC | STAGE5_ZONE1 | Cracks | | Not Inspected |
| | | | | . |

ENGINE1 SN001

ENDOSCOPE INSPECTION REPORT CREATING APPARATUS, CREATING METHOD OF ENDOSCOPE INSPECTION REPORT AND STORAGE MEDIUM

BACKGROUND OF THE INVENTION

1. Field of the Invention

The present invention relates to an endoscope inspection report creating apparatus, a creating method of an endoscope inspection report and a storage medium.

2. Description of the Related Art

Conventionally, endoscope apparatuses have been widely used in the industrial field and the medical field. An endoscope apparatus has an insertion portion which has an image pickup unit provided at a distal end portion, and a user who is an inspector brings the distal end portion of the insertion portion close to an object, cases an image which is picked up by the image pickup unit at the distal end portion of the insertion portion to be displayed on a monitor, and can cause the image to be stored in a storage device in accordance with necessity. For example, the user can connect the storage device such as a USB memory to a main body and can store an endoscopic image in the storage device.

In a conventional endoscope apparatus, as disclosed in Japanese Patent Application Laid-Open Publication No. 2003-9057, a DCIM directory is automatically created in a root directory in the storage device in accordance with the DCF standard, and endoscopic images are automatically stored under the directory.

When inspection using an endoscope apparatus is performed, the inspection report is created. The report includes an endoscopic image of the inspection target, determination information of the inspector and the like.

Conventionally, when an inspector creates an inspection report from an endoscopic image, the inspector creates the inspection report by pasting each endoscopic image in the report of a format determined in advance, writing the inspection result and the like by using document creation software or the like of a personal computer.

Further, for example, as described in Japanese Patent Application Laid-Open Publication No. 2006-276991, a setting method of a display/print screen for outputting the stored image information by using a template which is set or created in advance when the image information is displayed or printed is proposed.

SUMMARY OF THE INVENTION

An endoscope inspection report creating apparatus of one aspect of the present invention includes a file name reading section that reads file names of a plurality of endoscopic images, a file name of each of the endoscopic images including inspection result information separated with use of a predetermined symbol or character, and a report creating section that creates a predetermined report by writing the inspection result information which is included in each of the file names read by the file name reading section in each predetermined position in the predetermined report by associating the inspection result information with the endoscopic image of each of the read file names.

BRIEF DESCRIPTION OF THE DRAWINGS

FIG. 16 is a view for explaining a display example of an inspected folder which does not include an endoscopic image and an uninspected folder in the report, according to the embodiment of the present invention.

DETAILED DESCRIPTION OF THE PREFERRED EMBODIMENT

Hereinafter, an embodiment of the present invention will be described with reference to the drawings.
(Entire Configuration)

Figure 1:
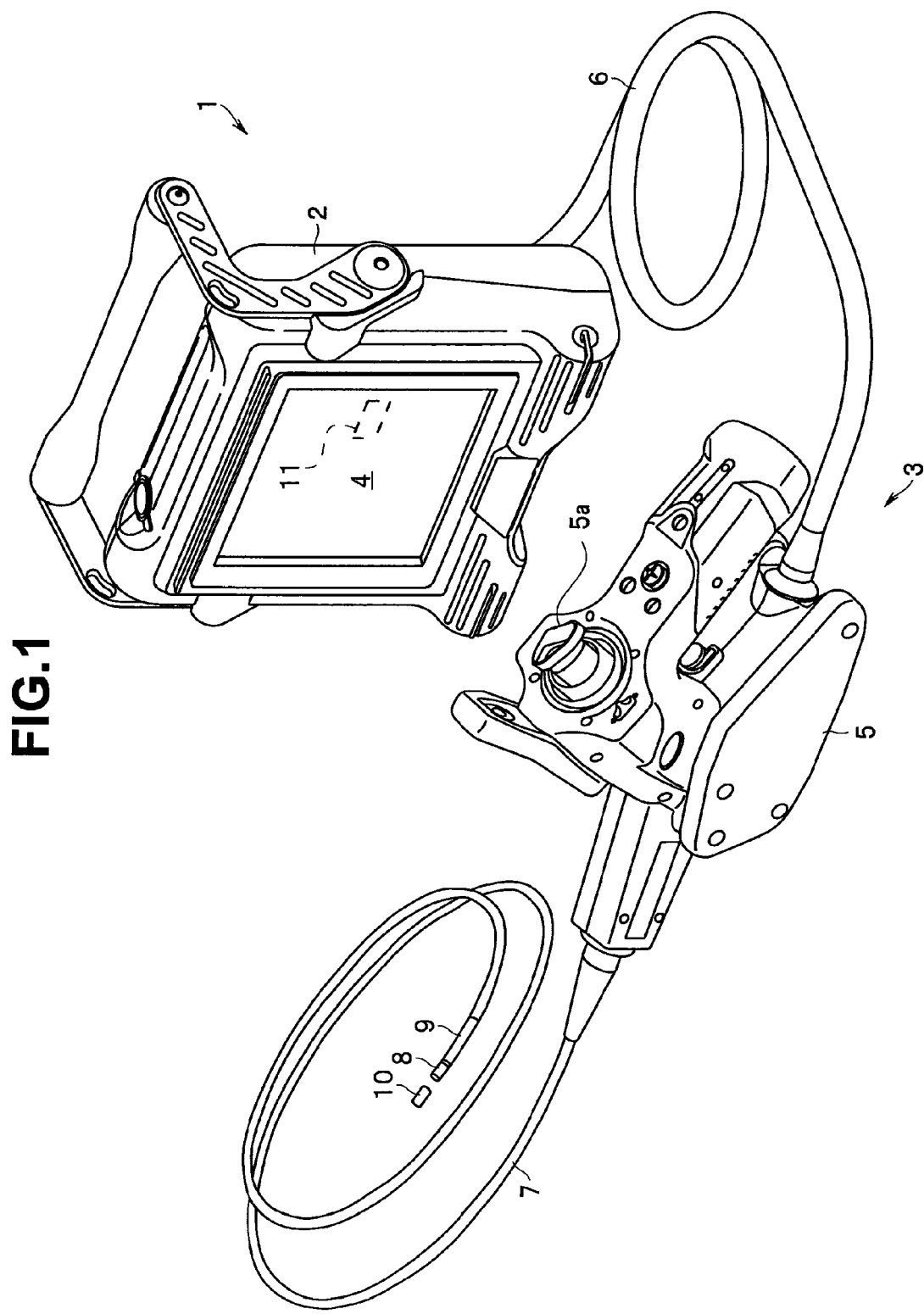
FIG. 1 is an external configuration view of an endoscope apparatus according to an embodiment of the present invention.

First, based on FIG. 1, a configuration of an endoscope apparatus according to the present embodiment will be described. FIG. 1 is an external configuration view of the endoscope apparatus according to the present embodiment.

Figure 2:
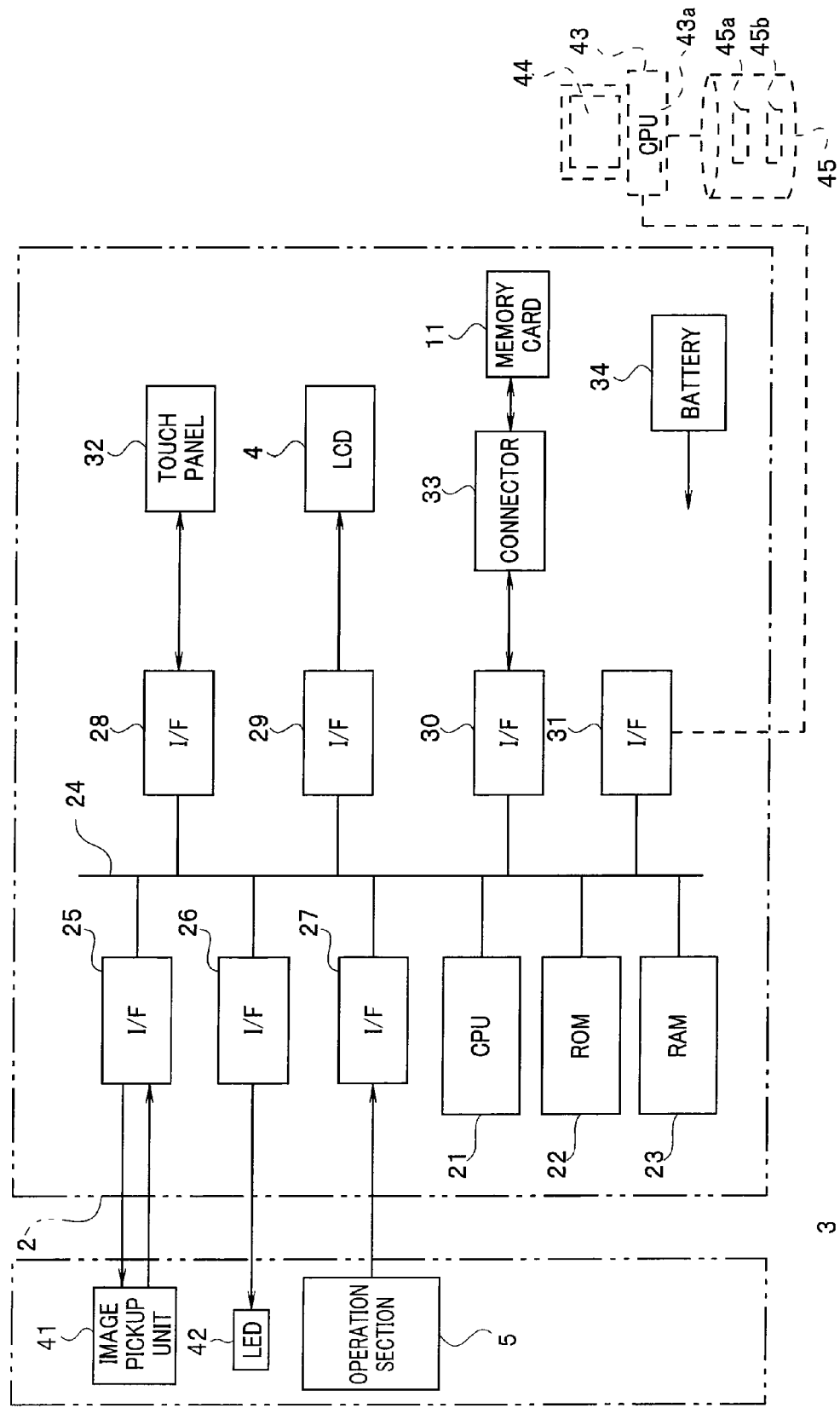
FIG. 2 is a block diagram for explaining a circuit configuration of an inside of a main body section 2 of an endoscope apparatus 1 according to the embodiment of the present invention.

As shown in FIG. 1, an endoscope apparatus 1 is configured to include a main body section 2 which is a main unit, and a scope unit 3 which is connected to the main body section 2. The main body section 2 has a liquid crystal display (hereinafter, abbreviated as an LCD) 4 as a display apparatus in which an endoscopic image, an operation menu and the like are displayed. The LCD 4 is a display section which displays an endoscopic image. As will be described later, the LCD 4 may be provided with a touch panel (FIG. 2). The scope unit 3 has an operation section 5, a universal cable 6 which is a connection cable for connecting the operation section 5 to the main body section 2, and an insertion portion 7 which includes a flexible insertion tube. The scope unit 3 is attachable to and detachable from the main body section 2. An image pickup unit (FIG. 2) which will be described later is contained in a distal end portion 8 of the insertion portion 7. The image pickup unit is configured by an image pickup device such as a CCD sensor or a CMOS sensor, for example, and an image pickup optical system such as a lens which is disposed at an image pickup surface side of the image pickup device. A bending portion 9 is provided at a proximal end side of the distal end portion 8. An optical adapter 10 is configured to be attachable to the distal end portion 8. The operation section 5 is provided with various operation buttons such as a freeze button, a storage instruction button (hereinafter, REC button), and an up, down, left and right (U/D/L/R) direction bending button.

A user can perform image pickup of an object, still image storage and the like by operating the various operation buttons of the operation section 5. Further, the user can select a storage destination folder by performing an operation of tilting a joystick 5*a* provided at the operation section 5 in any one of up, down, left and right directions, when the user performs change of the storage destination folder for an endoscopic image, which will be described later. Further, in the case of the configuration in which the touch panel is provided at the LCD 4, the user can give instructions of various operations of the endoscope apparatus 1 by operating the touch panel. More specifically, the touch panel configures an instruction section which gives an instruction on the operation content of the endoscope apparatus 1.

The image data of the endoscopic image which is picked up and obtained is inspection data of an inspection target, and is stored in a memory card 11, which is a storage medium. The memory card 11 is attachable to and detachable from the main body section 2.

In the present embodiment, image data is stored in the memory card 11 as a storage medium attachable to and detachable from the main body section 2, but the image data may be stored in a memory contained in the main body section 2.

The user can bring the distal end portion 8 of the insertion portion 7 to a site to be inspected of an inspection target, photograph the site to be inspected, obtains an endoscopic image, and can cause the endoscopic image to be displayed on the LCD 4. Further, as will be described later, the user can change the storage destination folder for endoscopic images while confirming the folder in the memory card 11 which stores the endoscopic images at the time of inspection, and operating the operation section 5 if necessary.

(Circuit Configuration)

FIG. 2 is a block diagram for explaining a circuit configuration of an inside of the main body section 2 of the endoscope apparatus 1.

The main body section 2 includes a central processing apparatus (hereinafter, called a CPU) 21, a ROM 22 and a RAM 23, which are connected to one another through a bus 24. Further, a plurality of various interfaces (hereinafter, called I/Fs) 25 to 31 are connected to the bus 24. The I/F 25 is a drive and receiving circuit for performing transmission of a drive signal to an image pickup unit 41 of the scope 3, and reception of an image pickup signal from the image pickup unit 41. The I/F 26 is a drive circuit for transmitting a drive signal to an LED 42 as an illumination section.

The I/F 27 is a circuit for receiving various operation signals from the operation section 5. Various operation signals from the operation section 5 include an operation signal of the joystick 5*a*. In the case of the configuration in which the touch panel 32 is provided at the LCD 4, the I/F 28 is provided as a circuit for receiving a drive signal to the touch panel 32 and an operation signal from the touch panel 32. The I/F 29 is a circuit for supplying an image signal to the LCD 4.

The I/F 30 is a circuit for performing write of an image signal to the memory card 11 and read of an image signal from the memory card 11. The I/F 30 is connected to the memory card 11 via a connector 33 provided at the main body section 2. The memory card 11 is detachably fitted to the connector 33.

The I/F 31 is a circuit for connecting a personal computer (hereinafter, called a PC) 43, which is an external device, to the main body section 2. The PC 43 is connected to the main body section 2 via a connector not illustrated, and the main body section 2 can exchange data with the PC 43 via the I/F 31 which is connected to the connector.

The PC 43 has a CPU 43*a* and a monitor 44, and a storage device 45 is connected to the PC 43. In the storage device 45, a report creation program 45*a* which will be described later is stored, and the report which is created by the report creation program 45*a* is displayed on the monitor 44, or outputted by a printer not illustrated. The storage device 45 further includes a template storage section 45*b* which stores a template which is used at a time of report creation which will be described later.

The main body section 2 contains a battery 34 in an inside thereof, and the battery 34 supplies power supply to various circuits in the main body section 2.

Each of the I/Fs operates under control of the CPU 21. When the endoscope apparatus 1 is actuated, the CPU 21 outputs various drive signals to the image pickup unit 41 via the I/F 25, and the image pickup unit 41 outputs an image pickup signal to the CPU 21. The CPU 21 outputs a drive instruction signal for the LED 42 to the I/F 26, and the LED 42 is driven by the output of the I/F 26, and illuminates the object, as a result of which, a live image is displayed on the LCD 4.

Since the operation section 5 is connected to the CPU 21 via the I/F 27, the operation section 5 supplies, to the CPU 21, various operation signals indicating the operation contents by the user to the operation section 5. When the user depresses the freeze button as will be described later, the CPU 21 generates a still image based on the image pickup signal from the image pickup unit 41, and when the user further depresses the REC button, the image data of the still image is stored in the memory card 11. Since the still image by freeze is displayed on the LCD 4, the user can confirm the still image, and when the user stores the still image, the user depresses the REC button.

(Folder Configuration)

A user can create an optional folder in the memory card 11. For example, the user creates a plurality of folders having a hierarchical structure in the memory card 11 by using a PC before endoscope inspection. More specifically, the user can create a plurality of folders of desired folder names under "root", and can cause each of the folders to store endoscopic images. Further, folders can be further created under the upper folders. That is to say, the user can create the folders having a hierarchical structure in the storage medium. Subsequently, as will be described later, the user can store, in a desired folder, the endoscopic image which is picked up and obtained by the image pickup unit 41 of the scope 3.

Figure 3:
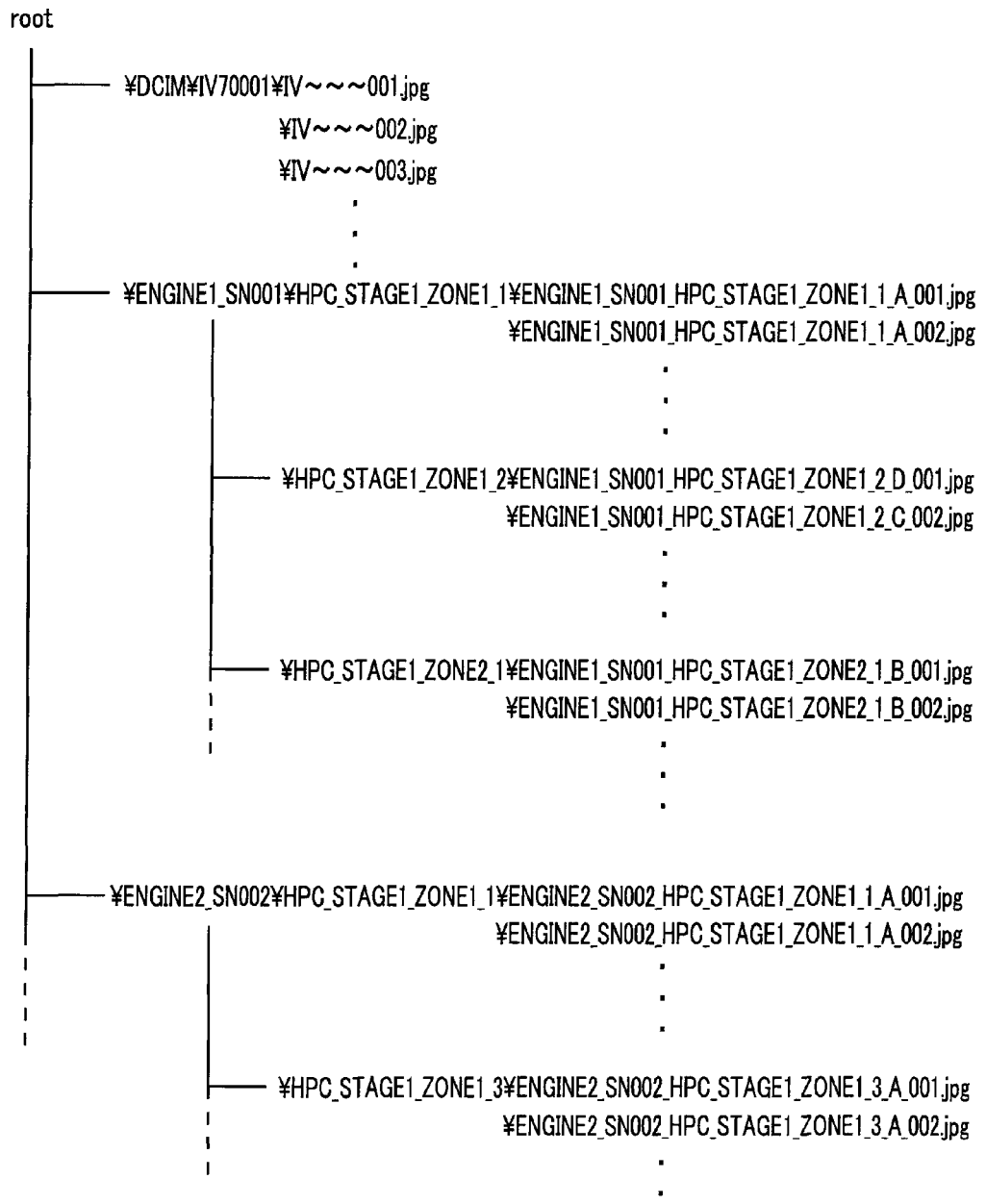
FIG. 3 is a diagram for explaining an example of a folder of a hierarchical structure according to the embodiment of the present invention.

FIG. 3 is a diagram for explaining an example of folders of a hierarchical structure. FIG. 3 schematically expresses respective folders and files included in the folders in order to explain the folders of a hierarchical structure, and here, FIG. 3 shows the example of the folder having two hierarchical layers, that is, two levels.

As shown in FIG. 3, the folder of "DCIM" is located under "root", and a lower folder named "IV70001" is located under the folder of "DCIM".

Further, a folder of "ENGINE1_SN001" is created under "root", and three lower folders named "HPC_STAGE1_ZONE1_1", "HPC_STAGE1_ZONE1_2", and "HPC_STAGE1_ZONE2_1" are created under the folder of "ENGINE1_SN001".

Furthermore, under "root", a folder of "ENGINE2_SN002" is also created, and under the folder of "ENGINE2_SN002", two lower folders named "HPC_STAGE1_ZONE1_1" and "HPC_STAGE1_ZONE1_3" are created.

"ENGINE1" and "ENGINE2" in "ENGINE1_SN001" and "ENGINE2_SN002" represent, for example, engine names, "SN001" and "SN002" represent serial numbers and the like, and "ENGINE1_SN001" and "ENGINE2_SN002" respectively represent inspection target information.

The three folders of "DCIM", "ENGINE1_SN001" and "ENGINE2_SN002" of the upper hierarchical layer are the folders of the same hierarchical layer. The folder of "ENGINE1_SN001", and the folders of "HPC_STAGE1_ZONE1_1 and "HPC_STAGE1_ZONE1_2" are the folders of the hierarchical layers different from each other, and the folder of "ENGINE2_SN002" and the folders of "HPC_STAGE1_ZONE1_1" and "HPC_STAGE1_ZONE1_3" are of the hierarchical layers different from each other.

That is to say, the user creates a folder with an optional name in advance under "root" in the memory card 11. The user may perform the folder creating work with the outside apparatus such as the PC 43, or may perform the folder creating work by connecting a hardware keyboard to the endoscope apparatus 1 and operating the hardware keyboard. Further, the user may perform the folder creating work by operating a setting screen displayed on the LCD 4 and a software keyboard which is configured as GUI. Furthermore, in the case of the configuration in which the touch panel 32 is provided at the LCD 4, the user may perform the folder creating work by operating the touch panel 32 or the like, by using the setting screen displayed on the LCD 4. As will be described later, the user selects an optional folder from a plurality of folders which are created in advance in this manner as a storage destination folder for endoscopic images, and can store the obtained endoscopic images in the selected folder.

In the present embodiment, the number of the folder hierarchical layers is two, but the number of the folder hierarchical layers may be three or more, and further, as shown by the dotted lines in FIG. 3, the number of folders of the same hierarchical layer may be three or more. Further, the number of the folder hierarchical layers does not have to be always two or more, and the folder structure with only one hierarchical layer under "root" may be adopted.

Furthermore, in FIG. 3, two folders have the lower folder name of "HPC_STAGE1_ZONE1_1", but the upper folders of the two folders differ from each other, and therefore, there is no problem even if the two folders have the same folder name. Note that the same hierarchical layer, that is, in the same hierarchical layer, the same folder name cannot be given to a plurality of folders.

As shown in FIG. 3, a plurality of endoscopic images in a JPEG format are shown to be stored in three folders of "HPC_STAGE1_ZONE1_1", "HPC_STAGE1_ZONE1_2" and "HPC_STAGE1_ZONE2_1".

The file name included in each of the folders has a configuration in which a file mark and a serial number are added to the folder names of the upper and lower hierarchical layers. That is to say, the file name is "upper folder name_lower folder name_file mark_serial number.jpg".

For example, the folder name of "ENGINE1_SN001" of the upper folder and the folder name of "HPC_STAGE1_ZONE1" of the lower folder are connected with symbol "_" (under bar), the file mark "A" and the serial number "001" are further added, and the file name as "ENGINE1_SN001_HPC_STAGE1_ZONE1_A_001.jpg" is generated. The configuration of the file name will be described in more detail later.

(Screen Display)

Figure 4:
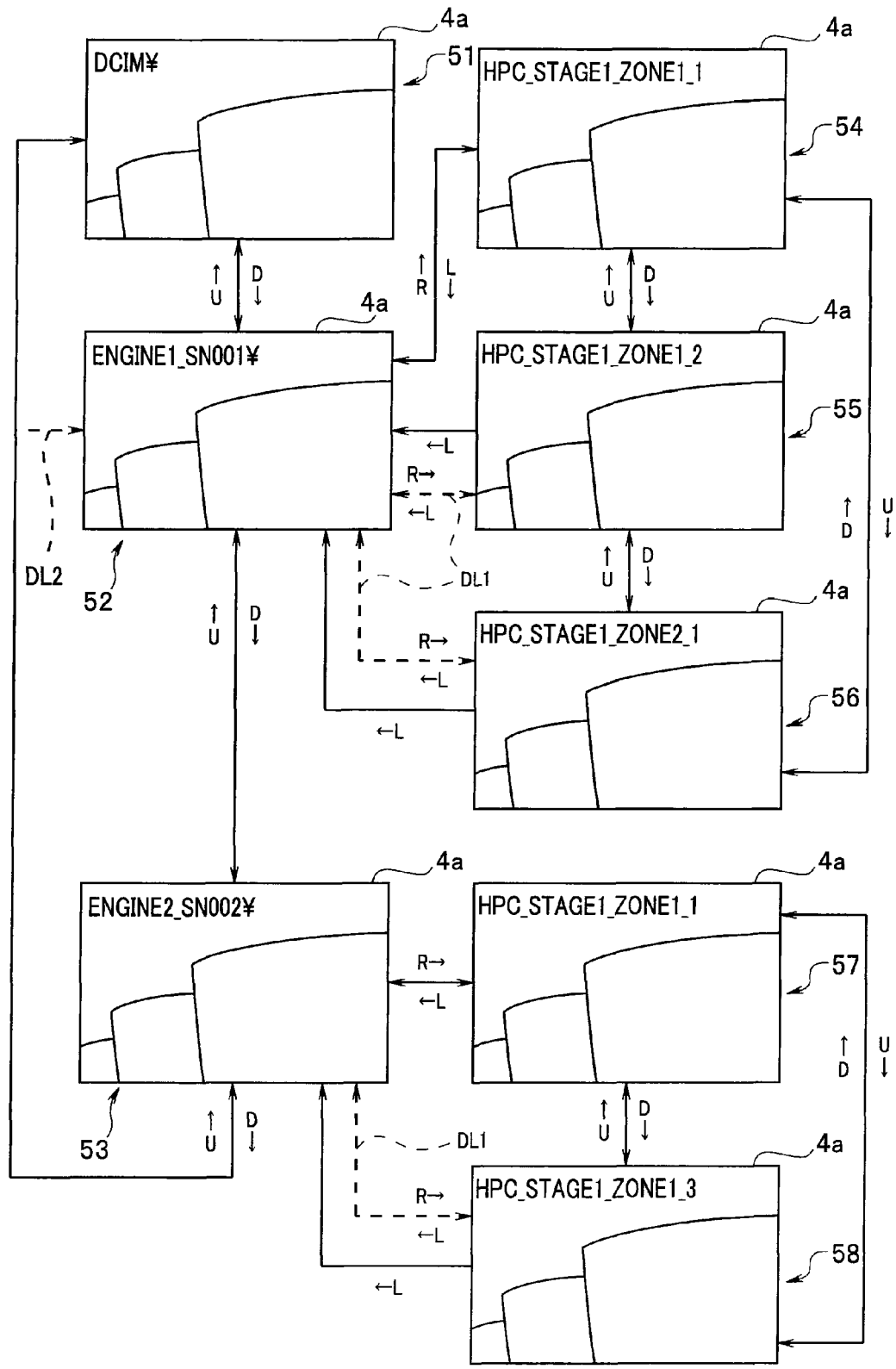
FIG. 4 is a diagram for explaining transition of screen display at a time of change of a storage destination folder, according to the embodiment of the present invention.

Next, screen display at a time of change of the storage destination folder will be described. FIG. 4 is a diagram for explaining a transition of screen display at the time of change of the storage destination folder.

When the power supply of the endoscope apparatus 1 is turned ON, a live image of a target picked up by the image pickup unit 41 is displayed on the screen of the LCD 4. The user performs inspection while watching the live image of the inspection target (turbine blade in FIG. 4) which is displayed on the screen.

On a screen 4a of the LCD 4, the live image, and the storage destination folder name for the image are displayed. After the power supply is turned ON, the "DCIM" folder under "root" is set in advance as the storage destination folder. Therefore, as shown in a screen 51, directly after the power supply is turned ON, "DCIM¥" is displayed on the screen 4a as the storage destination folder.

On the screen 51 of FIG. 4, information "DCIM¥" which indicates that the storage destination folder is the folder of "DCIM" is displayed at an upper left side of the screen 4a. On other screens 52 and the like, information including the storage destination folder names is also displayed at upper left sides of the screens 4a. However, the position of the information does not have to be the upper left side of the screen, and may be at an upper right side, for example.

Furthermore, in the case of FIG. 4, the mark "¥" is added to the folder names of the storage destination folders in the screens 51, 52 and 53 as the information indicating the storage destination folders. However, the mark "¥" does not have to be added.

Further, in the case of FIG. 4, the information indicating the storage destination folder is the information including the folder name of the storage destination folder. However, it is sufficient only if the user can recognize and discriminate the storage destination folder. Accordingly, the information indicating the storage destination folder does not have to include all the folder names of the storage destination folder, and may include only the folder name of the hierarchical layer which is selected at present, for example.

When the user desires to store a still image in the desired folder which is created in advance, the user can select the folder by operating the joystick 5a. When the joystick 5a is tilted in any one of the directions of up (U), down (D), left (L) and right (R), the folder is selected from a plurality of folders of the hierarchical structure in accordance with the direction, and is set as the storage destination folder.

FIG. 4 expresses the screen transition when the storage destination folder is selected from folder groups, where the three folders are created under the folder of "ENGINE1_SN001" and the two folders are created under the folder of "ENGINE2_SN002" as shown in FIG. 3. The order of display of the storage destination folders in each of the hierarchical layers is set in advance so that display is performed in a predetermined order such as the order of the creation dates and times of folders, the alphabetic order of the folder names, and the like.

As shown in FIG. 4, when the joystick 5a is tilted down (that is, tilted in a D direction) from the state of the screen 51, the folder of "ENGINE1_SN001" which is the next folder (folder under the folder of "DCIM", in FIG. 3) of the same hierarchical layer is selected as the storage destination folder, and the screen transitions to the screen 52 from the screen 51.

When the joystick 5a is tilted up (that is, tilted in a U direction) in the state of the screen 52, the folder of "DCIM" which is the previous folder of the same hierarchical layer (folder which is upper from the folder of "ENGINE1_SN001", in FIG. 3) is selected as the storage destination folder, and the screen transitions to the screen 51 from the screen 52.

When the joystick 5a is tilted down (that is, tilted in the D direction) from the state of the screen 52, the folder of "ENGINE2_SN002" which is the next folder of the same hierarchical layer is selected as the storage destination folder, and the screen transitions to a screen 53 from the screen 52.

When the joystick 5a is tilted down (that is, tilted in the D direction) from the state of the screen 53, the folder of "DCIM" which is the first folder of the same hierarchical layer is selected as the storage destination folder, and the screen transitions to the screen 51 from the screen 53.

Further, when the joystick 5a is tilted to the right (that is, tilted in an R direction) in the state of the screen 52, the folder of "HPC_STAGE1_ZONE1_1" which is the first folder (the uppermost folder in FIG. 3) of the lower hierarchical layer is selected as the storage destination folder, and the screen transitions to a screen 54 from the screen 52.

Furthermore, when the joystick 5a is tilted to the left (that is, tilted in an L direction) in the state of the screen 54, the folder of "ENGINE1_SN001" which is the folder of the upper hierarchical layer is selected as the storage destination folder, and the screen transitions to the screen 52 from the screen 54.

When the joystick 5a is tilted down (that is, tilted in the D direction) from the state of the screen 54, the folder of "HPC_STAGE1_ZONE1_2" which is the next folder of the same hierarchical layer is selected as the storage destination folder, and the screen transitions to a screen 55 from the screen 54.

When the joystick 5a is tilted up (that is, tilted in the U direction) in the state of the screen 55, the folder of "HPC_STAGE1_ZONE1_1" which is the previous folder of the same hierarchical layer is selected as the storage destination folder, and the screen transitions to the screen 54 from the screen 55.

When the joystick 5a is tilted down (that is, tilted in the D direction) from the state of the screen 55, the folder of "HPC_STAGE1_ZONE2_1" which is the next folder of the same hierarchical layer is selected as the storage destination folder, and the screen transitions from the screen 55 to a screen 56.

Further, when the joystick 5a is tilted up (that is, tilted in the U direction) in the state of the screen 54, the folder of "HPC_STAGE1_ZONE2_1" which is the last folder of the same hierarchical layer is selected as the storage destination folder, and the screen transitions from the screen 54 to the screen 56.

Further, when the joystick 5a is tilted down (that is, tilted in the D direction) in the state of the screen 56, the folder of "HPC_STAGE1_ZONE1_1" which is the first folder of the same hierarchical layer is selected as the storage destination folder, and the screen transitions from the screen 56 to the screen 54.

Furthermore, when the joystick 5a is tilted to the left (that is, tilted in the L direction) in the state of the screen 55 or 56, the folder of "ENGINE1_SN001" which is the folder of the upper hierarchical layer is selected as the storage destination folder, and the screen transitions to the screen 52 from the screen 55 or 56.

Screen transition among the folder of "ENGINE2_SN002" and the two lower folders "HPC_STAGE1_ZONE1_1" and "HPC_STAGE1_ZONE1_3" is performed among the screens 53, 57 and 58 similarly to the screen transition of the screens 52, 54, 55 and 56, as shown in FIG. 4.

Accordingly, the user can confirm the storage destination folder while watching the live image, and can easily perform change.

In the case of FIG. 4, when the joystick 5a is tilted to the right (that is, tilted in the R direction) in the state of the screen 52 or 53, after the screen transitions to the screen 52 or 53 from the screen 55, 56 or 58, the screen transitions to the screen 54 or 57 from the screen 52 or 53 so that the folder of "HPC_STAGE1_ZONE1_1" which is the first folder of the lower hierarchical layer is selected as the storage destination folder. However, when the joystick 5a is tilted to the right (that is, tilted in the R direction) in the state of the screen 52 or 53, after the screen transitions to the screen 52 or 53 from the screen 55, 56 or 58, the screen 55, 56 or 58 may be displayed as shown by the dotted line DL1 in FIG. 4. To this end, the folder data of the transition screen is stored in the RAM 23, and the CPU 21 controls the screen display to display a folder before the transition.

In the case of FIG. 4, the folder of "DCIM" is selected or set as the storage destination folder by default, but a predetermined folder in the folder of the uppermost hierarchical layer other than the folder of "DCIM", for example, the folder of "ENGINE1_SN001" as the first folder, may be selected by default.

Furthermore, when the folder is shifted to the folder of the same hierarchical folder in the uppermost hierarchical layer, the folder may be selected only among the folders other than "DCIM". In FIG. 4, when the joystick 5a is tilted down (that is, tilted in the D direction) in the state of the screen 53 as shown by the dotted line DL2, the screen may be made to transition to the screen 52. Then, when the joystick 5a is tilted up (that is, tilted in the U direction) in the state of the screen 52, the screen may be made to transition to the screen 53.

In the present embodiment, only the folder name of the hierarchical layer which is selected at present is displayed on the screen, but, for example, when the folder name of the lower hierarchical layer is displayed, the folder name of the hierarchical layer upper from the folder may be displayed in combination. At this time, the folder name in the screen 54, for example, is "ENGINE1_SN001¥HPC_STAGE1_ZONE1_1".

(Change Processing of Storage Destination Folder)

Figure 5:
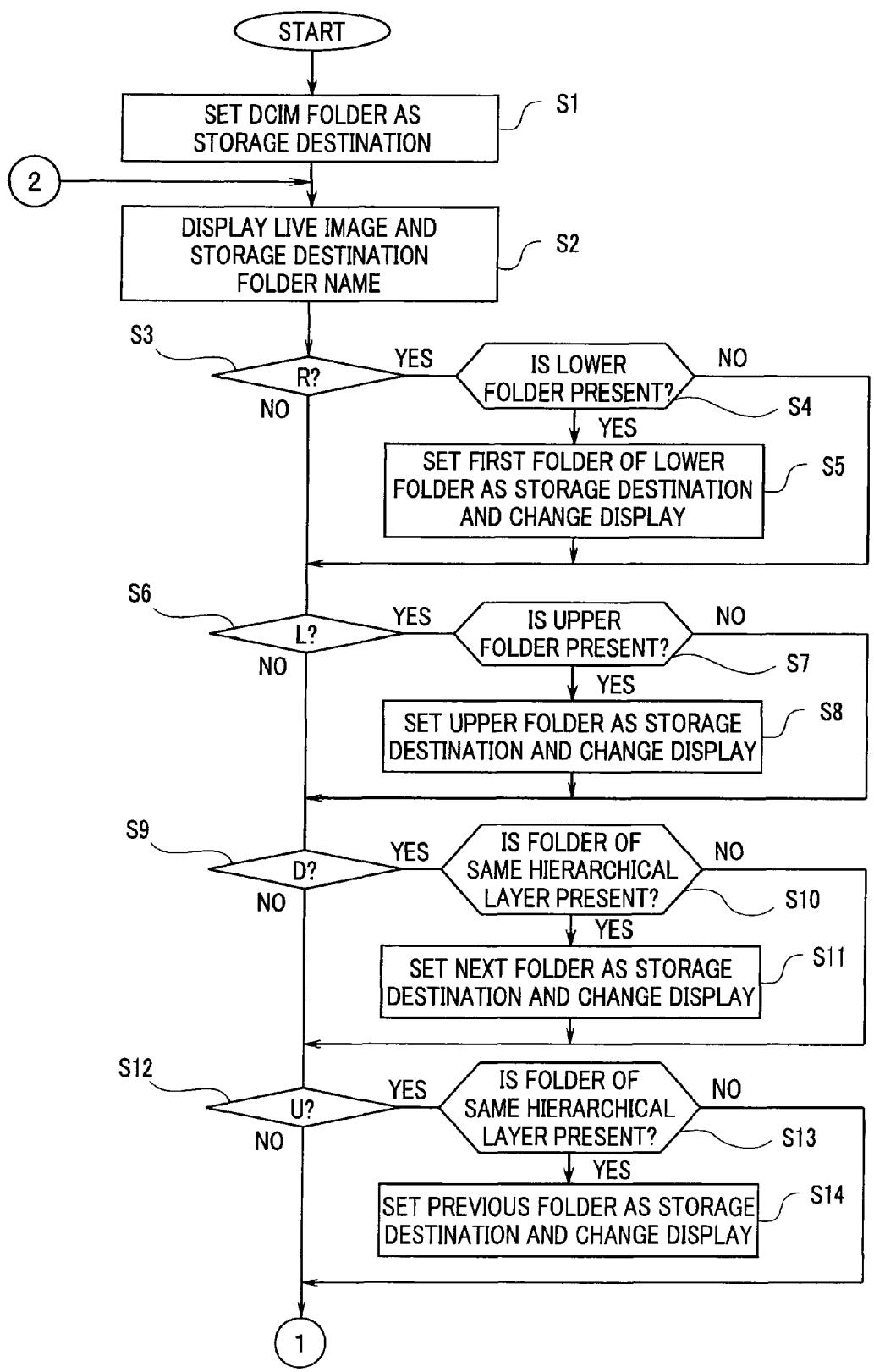
FIG. 5 and FIG. 6 are flowcharts showing an example of a flow of change processing of the storage destination folder according to the embodiment of the present invention.
Figure 6:
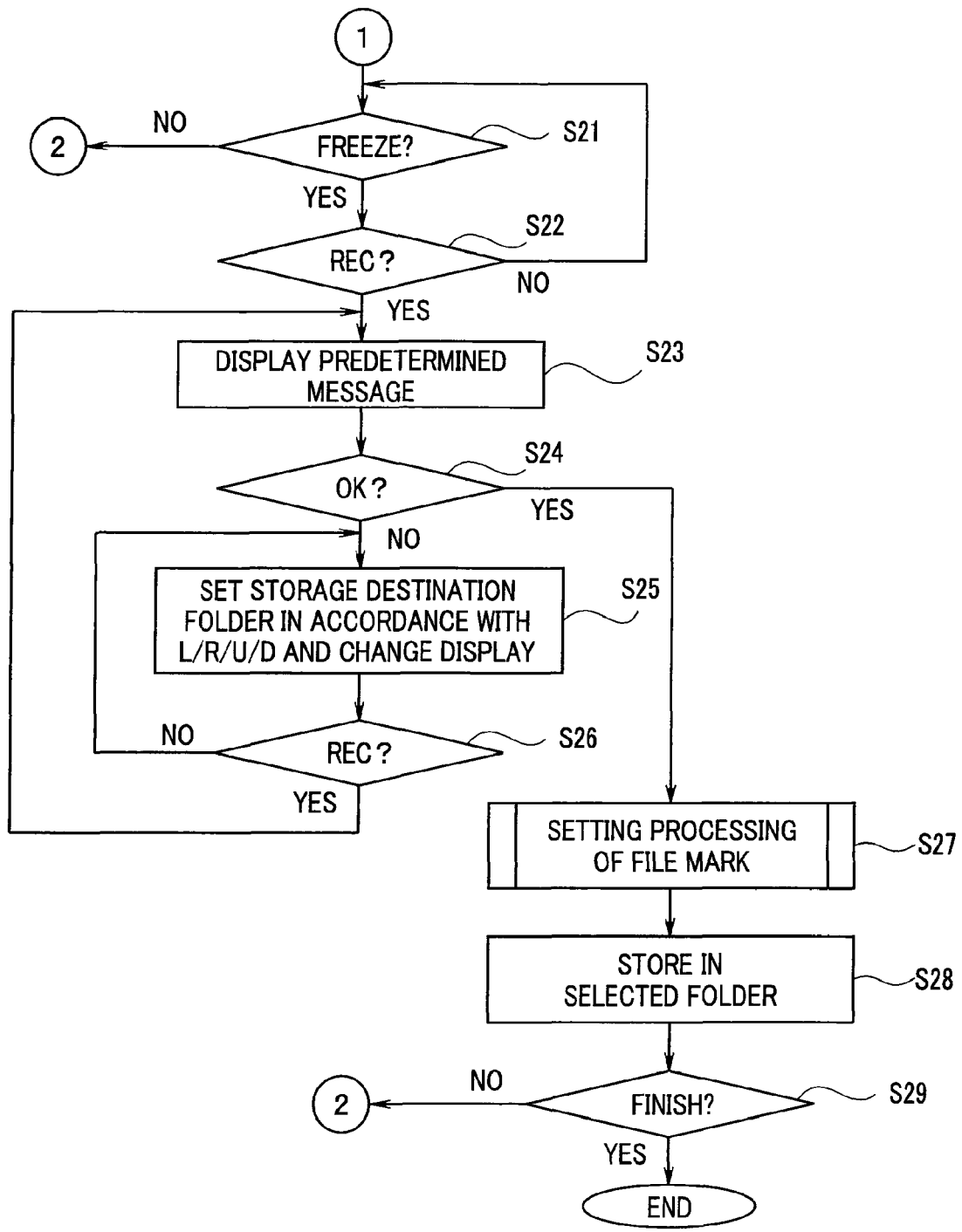

Next, change processing of the aforementioned storage destination folder will be described. FIG. 5 and FIG. 6 are flowcharts showing an example of a flow of the change processing of the storage destination folder.

First, when the power supply of the endoscope apparatus 1 is turned ON, the CPU 21 sets the folder "DCIM", which is the folder determined in advance as default, as the storage destination folder, after executing various kinds of initial processing (S1). The set data is stored in a predetermined storage region of the RAM 23, for example, as the set data of the storage destination folder in image storage processing which the endoscope apparatus has.

Thereafter, the CPU 21 displays a live image and the storage destination folder name on the screen 4a of the LCD 4 as the screen 51, based on the image pickup signal from the image pickup unit 41 (S2). The processing of S2 configures a storage destination folder information display section which displays the information indicating the storage destination folder in the state in which the endoscopic image is displayed in the display section.

Next, the CPU 21 determines whether or not the joystick 5a is tilted in the right (R) direction (S3), and when the joystick 5a is tilted in the right (R) direction (S3: YES), the CPU 21 determines whether or not the present storage destination folder has a lower folder (S4).

When a lower folder which is of a different hierarchical layer is absent (S4: NO), the processing returns to S3. When the lower folder is present (S4: YES), the CPU 21 sets the first folder of the lower folder as the storage destination folder, and changes the display of the storage destination folder name in the screen 4a (S5). Since the information of the storage destination folder is stored in the predetermined storage region of the RAM 23 as described above, the data of the predetermined storage region is rewritten with the data of the set, namely, changed folder.

For example, when the joystick 5a is tilted in the right (R) direction in the state in which the "ENGINE1_SN001" folder is the storage destination folder (screen 52), the "HPC_STAGE1_ZONE1__1" folder which is the first folder of the lower hierarchical layer is set as the storage destination folder. That is to say, the screen transitions from the screen 52 to 54.

A lower folder which is automatically created in accordance with the DCF standard is present in the "DCIM" folder, but the lower folder is not recognized. As a result, the folder of "DCIM" is set as the storage destination folder directly after the power supply is turned ON, but even if in this state (that is, the state of the screen 51), the joystick 5a is tilted in the right (R) direction, the CPU 21 determines that the lower folder is absent (S4: NO).

In the case of NO in S3, and after the processing of S5, the CPU 21 determines whether or not the joystick 5a is tilted in the left (L) direction (S6), and when the joystick 5a is tilted in the left (L) direction (S6: YES), the CPU 21 determines whether or not an upper folder of the present storage destination folder is present (S7).

When the upper folder which is of a different hierarchical layer is absent (S7: NO), the processing returns to S6. When the upper folder of the present storage destination folder is present (S7: YES), the CPU 21 sets the upper folder as the storage destination folder, and changes display of the storage destination folder name in the screen 4a (S8).

Since the "DCIM" folder, the "ENGINE1_SN001" folder and the "ENGINE2_SN002" do not have an upper folder, the CPU 21 determines that the upper folder is absent even if the joystick 5a is tilted in the left (L) direction in the states of the screens 51, 52 and 53 (S7: NO). Accordingly, in this case, the screens 51, 52 and 53 do not change.

In the case of NO in S6, and after the processing of S8, the CPU 21 determines whether or not the joystick 5a is tilted in the down (D) direction (S9). When the joystick 5a is tilted in the down (D) direction (S9: YES), the CPU 21 determines whether or not the folder of the same hierarchical layer as the present storage destination folder is present (S10).

When the folder of the same hierarchical layer is absent (S10: NO), the processing returns to S9. When the folder of the same hierarchical layer as the present storage destination folder is present (S10: YES), the CPU 21 sets the next folder of the same hierarchical layer as the storage destination folder, and changes display of the storage destination folder name in the screen 4a (S11).

For example, when the joystick 5a is tilted in the down (D) direction in the state in which the "DCIM" folder is the storage destination folder (state of the screen 51), the "ENGINE1_SN001" folder which is the next folder of the same hierarchical layer is set as the storage destination folder. That is to say, the screen transitions from the screen 51 to 52. Further, when the joystick 5a is tilted in the down (D) direction, the "ENGINE2_SN002" folder which is the next folder of the same hierarchical layer is set as the storage destination folder. That is to say, the screen transitions from the screen 52 to 53. Further, when the joystick 5a is tilted in the down (D) direction, the "DCIM" folder which is the first folder of the same hierarchical layer is set as the storage destination folder display of the storage destination folder in the screen 4a is changed since the next folder of the same hierarchical layer is absent. Then, the screen transitions from the screen 53 to 51.

In the same manner, if the joystick 5a is tilted in the down (D) direction in the state of the screen 54 in which the "HPC_STAGE1_ZONE1__1" folder is set as the storage destination folder, the screen transitions from the screen 54 to the screen 55 in which the "HPC_STAGE1_ZONE1__2" folder is set as the storage destination folder. Further, when the joystick 5a is tilted down in the down (D) direction in the state of the screen 55, the screen transitions from the screen 55 to the screen 56 in which the "HPC_STAGE1_ZONE2__1" folder is set as the storage destination folder. Further, when the joystick 5a is tilted in the down (D) direction in the state of the screen 56, the "HPC_STAGE1_ZONE1__1" folder which is the first folder of the same hierarchical layer is set as the storage destination folder since the next folder of the same hierarchical layer is absent. That is to say, the screen transitions from the screen 56 to 54.

In the case of NO in S9, and after the processing of S11, the CPU 21 determines whether or not the joystick 5a is tilted in the up (U) direction (S12). When the joystick 5a is tilted in the up (U) direction (S12: YES), the CPU 21 determines whether or not the folder of the same hierarchical layer as the present storage destination folder is present (S13).

When the folder of the same hierarchical layer is absent (S13: NO), the processing returns to S12. When the folder of the same hierarchical layer as the present storage destination folder is present (S13: YES), the CPU 21 sets the previous folder of the same hierarchical layer as the storage destination folder, and changes display of the storage destination folder name in the screen 4a (S14).

For example, when the joystick 5a is tilted in the up (U) direction in the state in which the "ENGINE1_SN001" folder is the storage destination folder (state of the screen 52), for example, the "DCIM" folder which is the previous folder of the same hierarchical layer is set as the storage destination folder. That is to say, the screen transitions from the screen 52 to 51. Further, when the joystick 5a is tilted in the up (U) direction, the "ENGINE2_SN002" folder which is the last folder of the same hierarchical layer is set as the storage destination folder since a previous folder of the same hierarchical layer is absent, display of the storage destination folder in the screen 4a is changed, and the screen transitions from the screen 51 to 53.

In the same manner, when the joystick 5a is tilted in the up (U) direction in the state of the screen 55 in which the "HPC_STAGE1_ZONE1__2" folder is set as the storage destination folder, the screen transitions from the screen 55 to the screen 54 in which the "HPC_STAGE1_ZONE1__1" folder is set as the storage destination folder. Further, when the joystick 5a is tilted in the up (U) direction in the state of the screen 54, the "HPC_STAGE1_ZONE2__1" folder which is the last folder of the same hierarchical layer is set as the storage destination folder, since the previous folder of the same hierarchical layer is absent. That is to say, the screen transitions from the screen 54 to 56.

The processing of S3 to S14 of the above configures a storage destination folder changing section which changes the storage destination folder in accordance with an operation of the operation section 5. More specifically, the processing of S3 to S14 configures the storage destination folder changing section which changes the storage destination folder in the state in which a live image is displayed, which is the state in which the endoscopic image is displayed on the LCD 4, and is the state in which the live image which is being picked up by the image pickup section provided at the insertion portion of the endoscope is displayed.

Returning to FIG. 5, in the case of NO in S12, and after the processing of S14, the CPU 21 determines whether or not the freeze button is depressed (FIG. 6, S21).

When the freeze button is not depressed (S21: NO), the processing returns to S2. When the freeze button is depressed (S21: YES), the CPU 21 determines whether or not the REC button is depressed (S22). The REC button is a button which performs instruction for storing the frozen image in the storage medium. When the freeze button is depressed, the CPU 21 generates a still image based on the image pickup signal from the image pickup unit 41, and displays the still image on the LCD 4.

The configuration may be adopted, in which when the freeze button is depressed in S21, the storage destination folder can be changed in the freeze state of a live image, as in S3 to S14 in the state in which a live image is displayed.

When the REC button is not depressed, the processing returns to S21. It is determined whether the freeze state is continued, in other words, whether the freeze state is unterminated or not. If the freeze state is terminated (S21: NO), the processing returns to S2.

If the REC button is depressed (S22: YES), the CPU 21 displays a predetermined confirmation message as shown in FIG. 7 on the screen 4a (S23).

Figure 7:
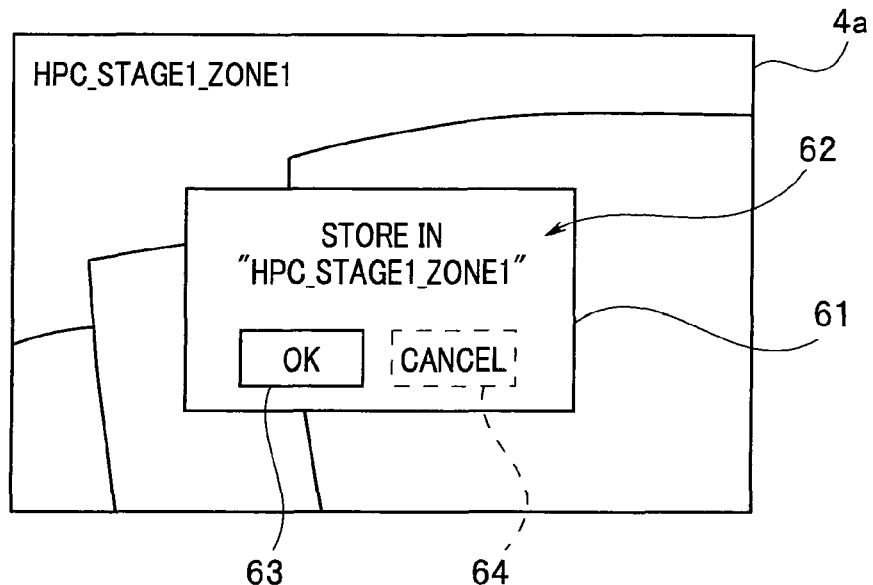
FIG. 7 is a view showing a display example of a confirmation message according to the embodiment of the present invention.

FIG. 7 is a view showing a display example of the confirmation message. On the screen 4a of the LCD 4, a still image by freeze is displayed, and on the screen, a predetermined confirmation message is displayed by a pop-up window 61. FIG. 7 is a display example in the case of the REC button being depressed in the display state of the screen 54, and a message 62 to the effect that "Store in "HPC_STAGE1_ZONE1__1"." is displayed in the window 61.

Further, the window 61 also includes an "OK" button 63 and a "cancel" button 64, and the user can select the "OK" button 63 or the "cancel" button 64 by performing a predetermined operation in the operation section 5. In FIG. 7, the "OK" button 63 is in a selected state as default, and therefore, the "OK" button 63 is displayed by being more emphasized than the "cancel" button 64.

The user selects the "OK" button 63 when the user stores the still image which is obtained by freeze in the folder shown in the confirmation message. However, when the user stores the still image which is obtained by freeze in the folder other than the folder shown in the confirmation message, the user selects the "cancel" button 64.

After S23, the CPU 21 determines whether or not the "OK" button 63 is depressed. When the "OK" button 63 is not depressed, that is, when the "cancel" button 64 is depressed (S24: YES), the CPU 21 erases the window 61 from the screen 4a, and the processing shifts to S25.

A still image by freeze, and the storage destination folder name which is set at present are displayed on the screen 4a. The user can change the storage destination folder by operating the joystick 5a in the screen display state.

Figure 8:
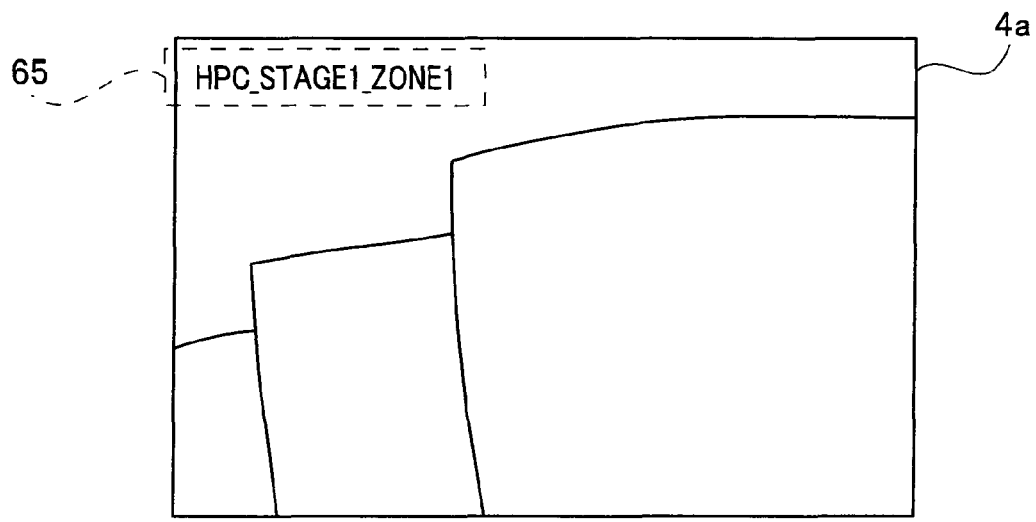
FIG. 8 is a view showing an example of a screen in a case in which the storage destination folder is changed in a state in which a still image is displayed, according to the embodiment of the present invention.

FIG. 8 is a view showing an example of the screen in a case in which the storage destination folder is changed in the state in which a still image is displayed. When the joystick 5a is operated in the state in which the still image displayed by freeze is displayed, the storage destination folder is changed in response to the operation, and only the folder name which is displayed in a storage destination folder display region 65 which displays the storage destination folder changes in the screen 4a, in response to the operation of the joystick 5a. Accordingly, the user displays a desired storage destination folder name on the storage destination folder display region 65 by operating the joystick 5a, and can change the storage destination folder.

The processing of S25 configures a storage destination folder changing section which changes a storage destination folder in accordance with an operation of the operation section 5, and also configures a storage destination folder information display section which displays information indicating the storage destination folder in the state in which an endoscopic image is displayed on the LCD 4.

In particular, the processing of S25 configures the storage destination folder changing section which can change the storage destination folder in the state in which a still image is displayed, which is the state in which an endoscopic image is displayed on the LCD 4, and the state in which the still image which is picked up and obtained by the image pickup section provided in the insertion portion of the endoscope is displayed.

As above, in the case of NO in S24, the CPU 21 changes the storage destination folder as shown in FIG. 4 in accordance with the tilting operation in the up, down, left and right directions of the joystick 5a, and the user selects and sets a desired folder as the storage destination folder, and changes display of the storage destination folder name in the screen 4a (S25).

It is determined whether or not the REC button is depressed again, in the state in which the storage destination folder is set and changed (S26). If the REC button is not depressed (S26: NO), the processing returns to S25.

If the REC button is depressed in S26 (S26: YES), the processing shifts to S23, and the CPU 21 displays a predetermined message for confirmation of the storage destination folder (S23).

When the storage destination folder is confirmed (S24: YES), setting processing of a file mark is performed (S27). The file mark is a predetermined mark which is added to the file name which is stored and functions as an identification symbol.

The file mark is optionally added by the user to show what image the stored image is. For example, in order to classify images into the kinds of "No problem (Accept)", "Replacement required (Reject)", "Repair required (Repair)", and "Re-inspection required (Re-Inspect)", file marks are added to file names. That is to say, the file mark is inspection result information which the user who is an inspector adds to an endoscopic image by watching the endoscopic image. Further, there is the kind of "Nothing". "Nothing" means no file mark (that is, no file mark can be added). Accordingly, addition of a file mark is performed according to a user's option.

Figures 9, 10:
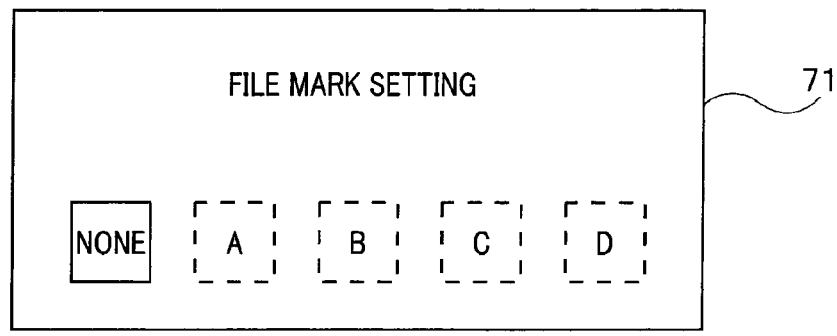
FIG. 9 is a view showing a display example of a file mark setting window according to the embodiment of the present invention.
FIG. 10 is a view for explaining a configuration of a file name according to the embodiment of the present invention.

FIG. 9 is a view of a display example of a file mark setting window in setting processing of a file mark.

A window 71 of FIG. 9 is also displayed as a pop-up window on a still image display screen as the window 61. The user can select any one of four kinds (five kinds if "nothing" indicating that nothing is added is included) by performing a predetermined operation in the operation section 5. In the case of FIG. 9, the four kinds of file marks, "A", "B", "C" and "D" can be added. Here, "A" corresponds to "No problem (Accept)", "B" corresponds to "Replacement required (Reject)", "C" corresponds to "Repair required (Repair)", and "D" corresponds to "Re-inspection required (Re-Inspect)".

Here, the file marks are single characters, but the file marks may be a plurality of characters, and character strings such as "ACCEPT" and "REPAIR".

The file name is made by addition of a file mark and a serial number to the folder name of the folder in which the file is stored, and therefore, the user can recognize the inspection result about the endoscopic image of a file, only by looking at the file mark in the file name. For example, if the file name is "HPC_STAGE1_ZONE1_1_A_001.jpg", the inspection result is found to be "No problem (Accept)", since the file mark is "A". If the file name is "HPC_STAGE1_ZONE1_1_B_001.jpg", the inspection result is found to be "Replacement required (Reject)", since the file mark is "B".

Accordingly, the user can judge the inspection site or the like from the folder name only by looking at the file name, and also judge the kind of the image.

In FIG. 9, when the window 71 is displayed as a pop-up window, "nothing" which indicates that nothing is added is in the selected state by default. Accordingly, if an operation of giving an instruction to finalize selection is performed in the state of FIG. 9, a file mark is not added to the file name. That is to say, the file name becomes "HPC_STAGE1_ZONE1_1_001.jpg" or the like.

The processing of S27 configures an identification symbol setting section which selects a file mark from a plurality of predetermined file marks and sets the file mark.

Returning to FIG. 6, in the case of YES in S24, the processing shifts to the setting processing of a file mark (S27), and file mark addition processing of including a file mark in a file name as described above is executed.

Thereafter, the CPU 21 stores an image in the selected or set storage destination folder (S28). That is to say, S28 configures a storage section which stores an endoscopic image in the storage destination folder which is set as the storage destination for an endoscopic image from a plurality of folders which are created in the memory card 11 in advance.

Further, in S28, when a still image of the endoscopic image which is acquired in response to the storage instruction from the operation section 5 is stored, the still image is stored in the set or changed storage destination folder after a predetermined confirmation message about the storage destination folder is displayed, and confirmation of the storage destination folder is performed.

Furthermore, in S28, the file mark which is set in S27 is added to the file name of the endoscopic image, and the endoscopic image is stored in the storage destination folder.

Subsequently, the CPU 21 determines whether or not an end instruction is given (S29), and when the end instruction is given (S29: YES), the processing ends. If the end instruction is not given (S29: NO), the processing shifts to S2.

In the aforementioned embodiment, the joystick is an operation section which is operable in the first direction which is a lateral direction, and the second direction which is a vertical direction orthogonal to the lateral direction. As for change of the storage destination folder, the storage destination folder is changed by hierarchical layer movement in the vertical direction of the hierarchical structure in response to the operation in the lateral direction, and the storage destination folder is changed by movement in the same hierarchical layer of the hierarchical structure in response to the operation in the vertical direction. Accordingly, by the operation of the joystick corresponding to the image of the hierarchical structure of the folder, the user can perform transition of the screen.

Furthermore, the operation section for changing the storage destination folder may be a so-called cruciform key, up, down, right and left keys, a button assigned with a function at the time of change of a folder or the like, in place of the joystick. Further, the operation section may be a cruciform key, up, down, left and right keys and the like generated by software, which are displayed on the screen.

Further, in the aforementioned embodiment, the joystick 5a is a dedicated joystick for change or selection of the storage destination folder. However, a joystick for use in a bending operation may be used as the operation device for selection of the storage destination folder under mode switching.

Furthermore, in the aforementioned embodiment, the information indicating the storage destination folder is displayed when a live image is displayed. However, the information indicating the storage destination folder may be displayed only when the freeze button is depressed.

As shown in FIG. 4, a user can confirm the storage destination folder when the user stores an endoscopic image, and can easily change the storage destination folder.

Further, the folder names are displayed on the screens shown in FIG. 4, FIG. 7, FIG. 8 or the like. There are causes where the user desires to confirm the meaning of the numerals since the character string of the inspection purpose in the folder name is numerals in the present embodiment. Thus, if the user superimposes a cursor on the character string indicating an inspection purpose, or performs a predetermined operation in the screen display state of FIG. 4 or the like, for example, the content of the meaning of the numerals may be displayed on a pop-up window. For example, in FIG. 7, when the cursor is moved to the position of the lowermost "1" of the folder name "HPC_STAGE1_ZONE1_1", the character string "Cracks" is displayed. Accordingly, the user who is an inspector can confirm the present inspection purpose, or can easily confirm whether the storage destination folder is the right storage destination folder.

(Configuration of File Name)

Here, a configuration of a file name will be described. FIG. 10 is a view for explaining the configuration of a file name. The file name is configured by five elements of first to fifth portions 81 to 85. The elements are separated by predetermined symbols.

An example of the file name of FIG. 10 is "ENGINE1_SN001_HPC_STAGE1_ZONE1_1_A_001.jpg". In the file name, the first "ENGINE1_SN001" is the portion 81 of the folder name of the first hierarchical layer, and corresponds to inspection target information including the character string indicating an inspection target shown by the engine name, the serial number and the like, for example.

The next "HPC_STAGE1_ZONE1_1" is the portion 82 of the folder name of the second hierarchical layer lower than the first hierarchical layer, and corresponds to inspection location information and inspection purpose information including character strings indicating the inspection location (or site) and the inspection purpose, for example. "HPC_STAGE1_ZONE1" corresponds to inspection location information indicating the inspection site or location. The last "1" which is separated by a symbol "_" (under bar) from "HPC_STAGE1_ZONE1" corresponds to inspection purpose information which is a character string (numeral in this case) showing the inspection purpose, that is, what inspection is performed, for example, whether inspection for a crack, or inspection for a surface defect is performed. In the present embodiment, the case of the last character (numeral) of the portion 82 of the folder name being "1" means crack inspection, "2" indicates a surface defect (flaking, or the like) inspection, and "3" indicates inspection for corrosion. That is to say, the last character of the portion 82 of the folder name corresponds to inspection purpose information.

As above, the first portion 81 and the second portion 82 include the folder names of the folders in which the file is stored. A plurality of files of endoscopic images are stored by being classified according to the inspection purposes since the folder names include the information of the inspection target, the inspection site and the inspection purpose. In other words, the folder configuration shows the content of inspection or the procedure of inspection.

Further, "A" in the file name corresponds to the portion 83 of the file mark. The file mark is inspection result information which includes a character showing the inspection result. The inspection result information is the information of the determination result of a user performing determination in the endoscope inspection. For example, if the file mark in the file name is "A", it means that the endoscopic image is the image with which the user determines the component as "no problem" without a crack in the component of the inspection target. If the file mark in the file name is "B", it means that the endoscopic image is the image with which the user determines the component as "replacement required" since the component has a crack. If the file mark in the file name is "C", it means that the endoscopic image is the image with which the user determines the component as "repair required" since the component has a crack. If the file mark in the file name is "D", it means that the endoscopic image is the image with which the user determines the component as "re-inspection required" since the component has a crack.

Further, "001" in the file name is the portion 84 of a serial number. When the endoscopic image is stored in the folder for the first time, the portion 84 of the serial number becomes "001", and the serial number is identification information which is incremented by "1" each time an endoscopic image is added thereafter.

In the file name, "jpg" is the portion 85 of an extension which is a character string for identifying the kind of the file.

As above, the inspection target information, the inspection location information, the inspection purpose information, the inspection result information and the serial number which respectively corresponds to the first to the fourth portions 81 to 84 included in the file name are separated from one another with use of the predetermined symbols (in this case, "_" (under bar)".

Here, the first to the fourth portions 81 to 84 are separated by "_" (under bars), but may be separated with use of other symbols such as "-" (hyphens) and "/" (slashes), or specific characters.

In the portions 81 and 82, "_" (under bars) which are the same as the separation symbols are used, but since the configurations of the character strings in each of the portions are determined in advance, the PC 43 can specify and extract each of the elements in the file name based on the predetermined configuration information of each of the portions when the PC 43 creates an inspection report, as will be described later.

As above, the endoscopic images are stored in the folders selected by the user, and the file name of each of the endoscopic images in each of the folders includes the folder name and the file mark.

(Configuration of Inspection Report)

Next, a configuration of an endoscope inspection report which is automatically created with use of the information of the file name will be described.

Figure 11:
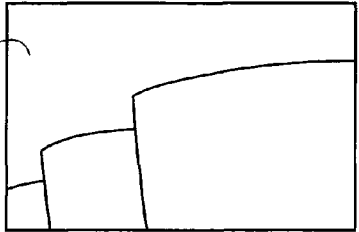
FIG. 11 is a view for explaining an example of a configuration of an endoscope inspection report according to the embodiment of the present invention.
Figure 11:
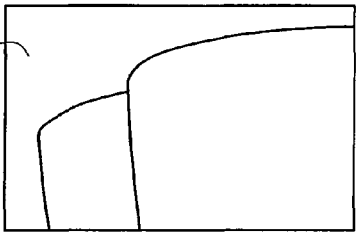
Figure 11:
Figure 11:
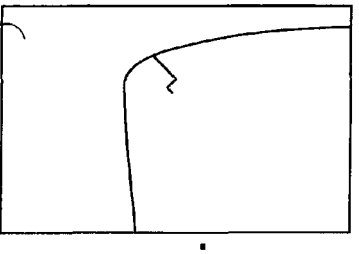

FIG. 11 is a view for explaining an example of the configuration of the endoscope inspection report. An endoscope inspection report (hereinafter, also simply called a report) 100 is displayed on a screen or printed. FIG. 11 shows the configuration of the report which is displayed on the screen or printed. The report 100 of the present embodiment is in a tabular format, and is configured to include five columns of an upper column 101 of an inspection location (Area), a lower column 102 of an inspection location (Block Location), a column 103 of an inspection purpose (Reason for Inspection), a column 104 of an inspection result (Outcome), and a column 105 of an endoscopic image (Picture). The report 100 is configured to further include a title section 106 which displays an inspection target.

The report 100 is created with use of the information of a file name. In the title section 106, "ENGINE1_SN001" is shown, which shows that the report relates to the inspection target "ENGINE1_SN001". The title section 106*n* corresponds to the character string of the first portion 81 of the file name.

In the example of FIG. 11, "HPC" is shown in the column 101, which indicates that the inspection location is "HPC". The column 101 corresponds to the character string of the first half portion of the second portion 82 of the file name.

In the column 102, "STAGE1_ZONE1" or the like is shown, which indicates that the inspection location is "STAGE1_ZONE1" or the like. The column 102 corresponds to the character strings at the central portion of the second portion 82 of the file name.

In the column 103, "Cracks" or the like is shown, which indicates that the inspection purpose is "Cracks" or the like, that is, inspection for cracks or the like. The column 103 corresponds to the character string of the latter half portion of the second portion 82 of the file name.

As will be described later, the character strings shown in the columns 101 to 103 are registered in advance in the predetermined template which is prepared in advance for each inspection target.

In the column 104, "Accept" or the like is shown, which indicates that the inspection result is "Accept (no problem)" or the like. The column 104 is generated based on the character string of the third portion 83 of the file name.

In the column 105, the endoscopic image corresponding to the file name is pasted.

In FIG. 11, an endoscopic image 111 which is determined as "Accept" (no problem) is shown in the report 100 as the result of inspection for cracks about the inspection location of "STAGE1_ZONE1" of "HPC", as an example. Likewise, an endoscopic image 112 which is determined as "Accept" (no problem) is also included in the report 100 as the result of inspection for cracks about the same inspection location ("STAGE1_ZONE1" of "HPC").

Further, an endoscopic image 113 which is determined as "Re-Inspect" (re-inspection required) as the result of inspection for a surface defect about the inspection location of "STAGE1_ZONE1" of "HPC" is shown in the report 100.

Furthermore, as the inspection result about another inspection location, an endoscopic image 114 which is determined as "Reject" (replacement required) as the result of inspection for cracks about the site of "STAGE1_ZONE2" of "HPC" is shown in the report 100.

That is to say, the endoscope inspection report shows the endoscopic image and the inspection result about the image in a tabular format for each inspection purpose of each inspection location.

(Creation Procedure of Inspection Report)

Next, a creation procedure of the report will be described.

A plurality of endoscopic images which are picked up and obtained by a user are stored in a plurality of folders in the memory card 11 as described above. The user connects the PC 43 to the endoscope apparatus 1, and creates the endoscope inspection report 100.

Since the PC 43 can read the information of the memory card 11 of the endoscope apparatus 1, the PC 43 executes the report creation program 45*a* under the instruction of the user, reads the information of the folders in the memory card 11, and creates the report. Accordingly, the PC 43 configures an endoscope inspection report creating apparatus. Since the memory card 11 is attachably and detachably connected to the endoscope apparatus 1, the user may directly connect the memory card 11 which is detached from the endoscope apparatus 1 to a predetermined interface of the PC 43 to enable the PC 43 to read the information of the folder, and create the report.

The user prepares the template of the report in advance for each inspection target of endoscope inspection. The template is created in advance by the user with use of the PC 43, and is stored in the template storage section 45*b* of the storage device 45.

Figure 12:
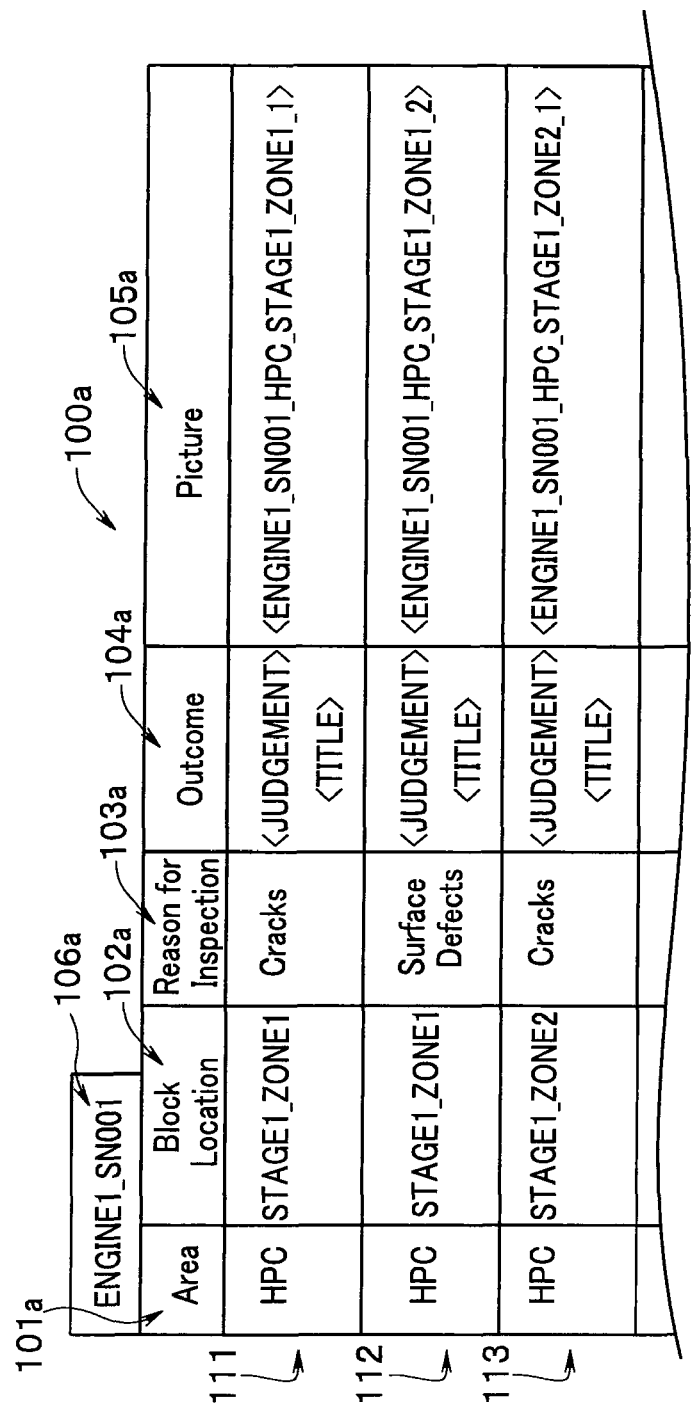
FIG. 12 is a view for explaining an example of a template 100a of a report according to the embodiment of the present invention.

FIG. 12 is a view for explaining an example of a template 100*a* of the report. FIG. 12 shows a configuration of the template 100*a* of the report about the inspection target "ENGINE1_SN001". The template of FIG. 12 is a template of the inspection target "ENGINE1_SN001", and therefore, at the position of the template 100*a* corresponding to the column 106 of the report, the character string of "ENGINE1_SN001" is written and set in advance.

Further, the inspection location of the inspection target is determined in advance, and therefore, at the respective positions of the template 100*a* corresponding to the columns 101 and 102 of the report, the character strings of "HPC" and "STAGE1_ZONE1" are set in advance.

In a column 104*a* of the inspection result (Outcome) of the template 100*a*, which corresponds to the column 104 of the report, "<JUDGEMENT>" is written, and the template 100*a* is defined so that the character string corresponding to the file mark is inputted.

Further, the data of an endoscopic image is configured such that an inspector can additionally input and store a comment about the image in the image data as additional information of the image. For example, if the endoscopic image is the data in an EXIF format, the user can store the comment of the inspector in a user comment tag or the like included in the data as metadata.

Thus, in the column 104*a*, "<TITLE>" is written, and the template 100*a* is defined so that the stored comment is inputted therein. Accordingly, the template 100*a* is defined by also having "<TITLE>" written in the column 104 in addition to "<JUDGEMENT>", as shown in FIG. 12. A comment is transcribed in the "<TITLE>" portion.

Since an endoscopic image is displayed in the column 105 of the report, "<ENGINE1_SN001_HPC_STAGE1_ZONE1_1>" is written in the column 105*a* of FIG. 12, and the template 100*a* is defined so that the endoscopic image is inputted therein.

As shown in FIG. 12, a template definition section 111 specifies the content of the template about the folder "HPC_STAGE1_ZONE1_1", a template definition section 112 specifies the content of the template about the folder "HPC_STAGE1_ZONE1_2", and a template definition section 113 specifies the content of the template about the folder "HPC_STAGE1_ZONE2_1".

As above, the content which is described in the report is defined for each folder in the template which is prepared in advance for each inspection target. Each template specifies respective predetermined positions of the inspection result information, the endoscopic image, and the inspection purpose information in a predetermined report. At the spot of the character string at the portion sandwiched by "<" and ">" in the template which is prepared in advance, the image data, the determination result, and the metadata of each of the files which are obtained by analysis are filled. As a result, the report is created based on the template as in FIG. 11, and screen display or printout of the report is enabled.

In the present embodiment, the example using the template which is defined so that the data obtained by analysis of the file/file name is filled therein is described. However, the template may be the one in which the rule is set to arrange the inspection target information, the inspection location information, the inspection purpose information, and the inspection result information separated by the predetermined symbols in one row for each file.

As above, the template for each inspection target is created in advance. The template information is stored in the template storage section 45*b* of the storage device 45. The report creation program 45*a* creates the report based on the template.

Next, creation processing of the report will be described. The endoscope inspection report is created by the report creation program 45*a* which is stored in advance in the storage device 45 of the PC 43.

Figure 13:
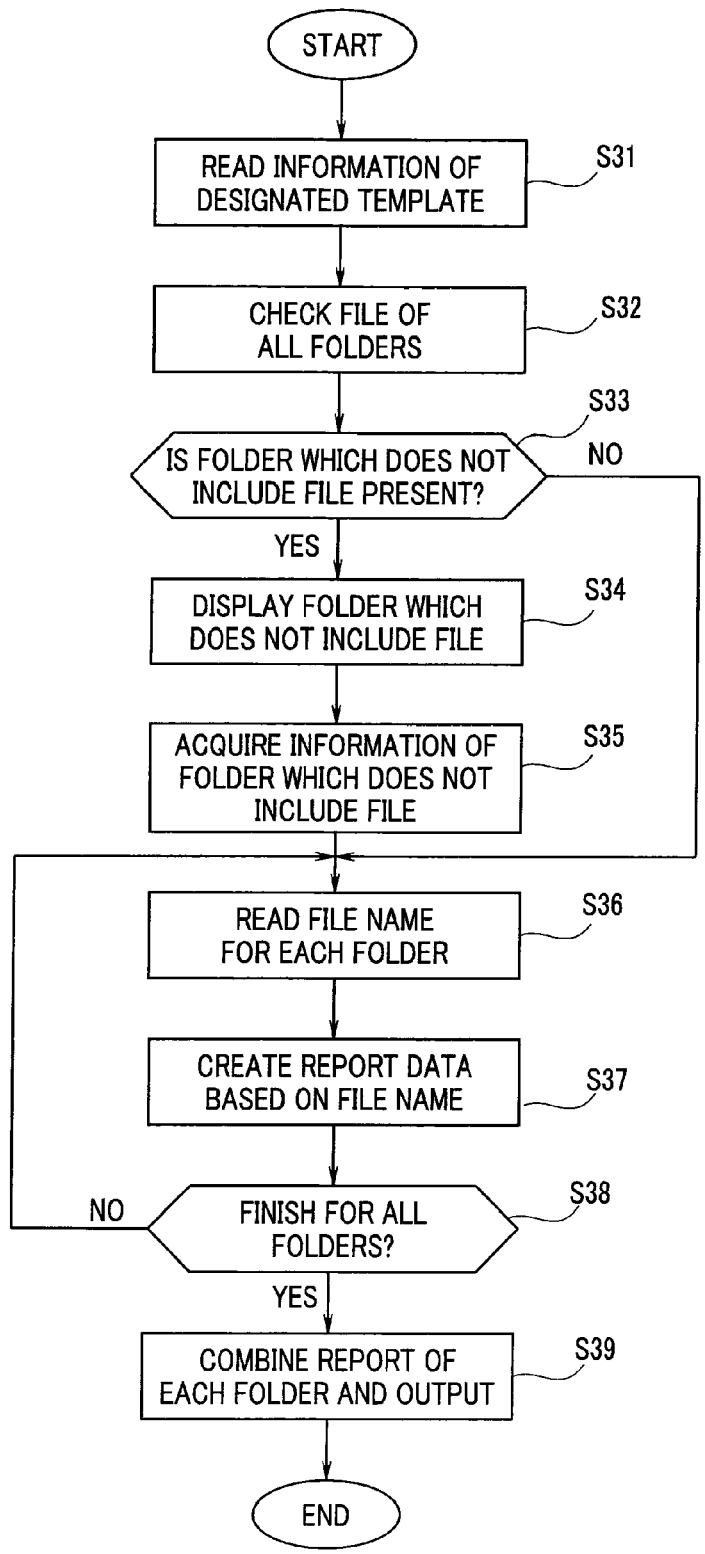
FIG. 13 is a flowchart showing an example of a flow of creation processing of the report according to the embodiment of the present invention.

FIG. 13 is a flowchart showing an example of a flow of the creation processing of the report.

Hereinafter, the creation processing of the report will be described with the example of the case in which the user performs endoscope inspection of "ENGINE1_SN001" which is the inspection target and the user creates a report by using the template 100*a* shown in FIG. 12 as a template.

When the user who is an inspector instructs the CPU 43*a* of the PC 43 about execution of the report creation program 45*a* by using input means such as a keyboard of the PC 43, execution of the processing of FIG. 13 is started. At this time, the user specifies the template for use in creation of the report.

First, the CPU 43*a* reads the information of the specified template (S31). The information of the template of FIG. 12 is read from the template storage section 45*b* of the storage device 45 of the PC 43.

Next, the CPU 43*a* checks presence or absence of the files of all the folders included in the inspection target for which the report is created (S32). For example, when the report of "ENGINE1_SN001" is created, whether or not files are present is checked for all the lower folders included in the folder of "ENGINE1_SN001" in S32. The processing of S32 configures a file presence/absence determining section which determines presence or absence of the files included in a respective plurality of folders.

Next, it is determined whether or not the folder which does not include a file is present (S33). When it is determined that the folder which does not include a file is present (S33: YES), the CPU 43*a* displays the folder which does not include a file on the screen of the monitor of the PC 43 (S34). At this time, addition of file marks may be determined with respect to the files of all the lower folders, and the files to which a file mark is not added may be displayed in combination.

Figures 14, 15:
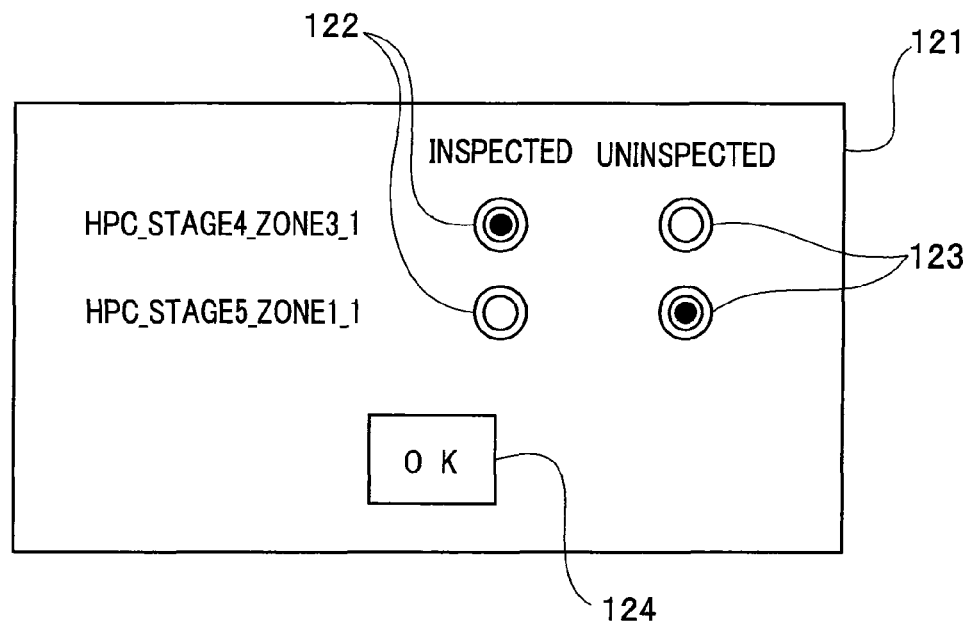
FIG. 14 is a view showing a display example of a pop-up window displaying folders which do not include a file, according to the embodiment of the present invention.
FIG. 15 is a diagram showing an example of a file mark correspondence table storing a character string to be written in a column 104a of the template 100a for each file mark, according to the embodiment of the present invention.

FIG. 14 is a view showing a display example of a pop-up window which displays the folders which do not include a file. FIG. 14 shows the example of the folder configuration differing from the example of FIG. 3, and shows the example in which when two folders "HPC_STAGE4_ZONE3_1" and "HPC_STAGE5_ZONE1_1" are present as the folders which do not include a file, in a plurality of folders included in the inspection target, the two folders are displayed in a pop-up window 121.

In the pop-up window 121 of the example of FIG. 14, as the folders which do not include a file, the two folders "HPC_STAGE4_ZONE3_1" and "HPC_STAGE5_ZONE1_1" are displayed.

In the pop-up window 121, check buttons 122 and 123 for the user to input whether the user did not pick up an image at all though the user performed inspection, or the user did not perform inspection yet are displayed, for each folder which does not include a file. Further, in the pop-up window 121, an "OK" button 124 is also displayed. The user can select any one of the check buttons 122 and 123 by specifying the check button by using the input means such as a mouse. FIG. 14 shows that since the user specifies that about the folder "HPC_STAGE4_ZONE3_1", inspection is already performed, the check button 122 is checked and the black circle is displayed, whereas since the user specifies that inspection is not performed yet with respect to the folder "HPC_STAGE5_ZONE1_1", the check button 123 is checked and the black circle is displayed.

When the user selects the "OK" button 124 after performing the above described check, the CPU 43a acquires the information of the folder which does not include a file, which is inputted by the user in the pop-up window 121 (S35).

In the case of NO in S33 and after the processing of S35, the CPU 43a reads the file names of each folder (S36), and creates data in the report by using the specified template, based on the information of the file name of each file in each folder (S37). More specifically, in the case of "ENGINE1_SN001" which is the inspection target, the CPU 43a reads each file in the folder "HPC_STAGE1_ZONE1_1" in the sequence of the serial number, and writes the character string indicating the inspection result in the column 104a based on the file mark in the file name of the read file, and further, pastes the endoscopic image of the file name on the column 105a.

As described above, the file mark is configured by one character here, and therefore, in the report, the inspection result information is converted and written in the column 104 so that the user can understand the inspection result information.

FIG. 15 is a diagram showing an example of a file mark correspondence table in which the character string to be written in the column 104a of the template 100a is stored for each file mark. The file mark correspondence table of FIG. 15 may be stored in the storage device 45, or may be defined in the report creation program 45a.

The file mark correspondence table 131 is a table which includes the file marks, and the character strings corresponding to the file marks, and is for converting the inspection result information. Accordingly, the CPU 43a determines the character string corresponding to the file mark in the file name with reference to the file mark correspondence table 131, and writes the character string in the column 104a of the template 100a.

For example, if the file mark in the file name is "A", the character string "Accept" corresponding to "A" is written in the column 104a of the template 100a. In the example of FIG. 11, the character string "Accept" corresponding to "A" is written in the column 104a, the character string "Reject" corresponding to "B" is written in the column 104a, and the character string "Re-Inspect" corresponding to "D" is written in the column 104a. That is to say, in S37, the inspection result information is converted into predetermined inspection result inscription information, and is written in the column 104a of the report 100a.

Further, as described above, when a comment is added to the file, the CPU 43a also writes the comment in the column 104a of the template 100a. FIG. 11 shows an example in which comments "Some Defects" and "Cracks" are displayed in the column 104.

The CPU 43a pastes the endoscopic image after performing processing of reducing the endoscopic image into a predetermined size so that the endoscopic image of the file which is read is suitably included in the column 105a.

As above, in S36, read of the file name of the endoscopic image in the folder is performed, and creation of the report data is performed based on the file name. Accordingly, S36 configures a file name reading section which reads the file names of a plurality of endoscopic images, with the file name of each of the endoscopic image including the inspection result information separated with use of a predetermined symbol or character. Further, S37 configures a report creating section which creates a predetermined report by writing the inspection result information included in each of the file names which are read by the file name reading section at respective predetermined positions in the predetermined report by associating the inspection result information with the endoscopic image of each of the file names which is read.

In the aforementioned template, the inspection purpose is determined in advance, and therefore, the character string of the inspection purpose information is set in the column 103a, but the character string indicating the inspection purpose may be generated from the inspection purpose information included in the portion 82 of the file name, and may be written therein. For example, when the inspection purpose information is "1", "1" is converted into the inspection purpose inscription information of "Cracks", and is written in the column 103a.

In the same manner, since in the aforementioned template, the inspection location is determined, the character strings of the inspection location information are set in the columns 101a and 102a, but the inspection location information included in the portions 81 and 82 of the file name is extracted, and the character strings of the extracted inspection location information may be written. For example, the respective character strings of "HPC" and "STAGE1_ZONE1" are extracted from the portions 81 and 82, and the two extracted character strings "HPC" and "STAGE1_ZONE1" are respectively written in the columns 101a and 102a.

The CPU 43a performs write of the determination result information in the column 104a of the template 100a, and paste of the endoscopic image of the file name onto the column 105a of the template 100a, based on the file name, with respect to each of the files included in the folder. The processing of S36 and S37 is performed with respect to all the files in one folder.

After the processing of S37 is finished, the CPU 43a determines whether or not execution of the above described processing is finished with respect to all the folders (S38). This is for executing the similar processing with respect to other folders after the processing of S36 and S37 with respect to one folder is finished when a plurality of folders included in the inspection target are present.

If the above described processing is not executed with respect to all the folders (S38: NO), the processing returns to S36, and the processing of S36 is executed with respect to the other folders for which the processing is not executed.

With respect to the folder with inspection finished and without including an endoscopic image, which is described in FIG. 14, the CPU 43a fills the characters of "No image" in the column 105, or fills the image with the characters of "NO PHOTO". Further, for the uninspected folder, the character of "Uninspected" is filled in the column 105.

FIG. 16 is a view for explaining a display example of the inspected folder which does not include an endoscopic image and the uninspected folder in the report. FIG. 16 is the display example about the folder shown in FIG. 14.

As shown in FIG. 16, as to the folder "HPC_STAGE4_ZONE3_1", an image 115 with the characters of "NO PHOTO" is pasted, and "Accept" is written in the column 104a. As for the folder "HPC_STAGE5_ZONE1_1", a character 116 of "Uninspected" is written in the column 105a. That is to say, when the folder which does not include a file is detected by S32, the file absence information indicating that the folder is the one that does not include a file is written in the report in S37. The file absence information is, for example, the characters of "No image", the image with the characters of "NO PHOTO", and the characters of "Uninspected".

As above, when processing for all the folders is finished (S38: YES), the contents of the respective columns 101a to 105a for each of the folders are combined and are generated as a separate file from the template 100a, and the report 100 shown in FIGS. 11 and 16 is outputted (S39). The data of the outputted report 100 is stored in the storage device 45, and subsequently displayed on the monitor 43, or outputted to a printer.

That is to say, a plurality of endoscopic images which are obtained by the endoscope inspection are stored in a plurality of folders which are separated according to the inspection target information, and in S36 and S37, the endoscopic image and the inspection result information of each of the file names are written in the predetermined position in the report for each folder.

Accordingly, when the user specifies the folder of the inspection target, and executes the report creation program 45a in the PC 43, after performing endoscope inspection, the user can automatically create the endoscope inspection report as shown in FIGS. 11 and 16.

According to the aforementioned embodiment, the user can easily create the endoscope inspection report without performing complicated work of looking at each of endoscopic images, pasting the endoscopic image on the report in a predetermined format, and copying or inputting the determination result of the image in addition as with the conventional apparatus.

In the above example, the endoscope inspection report is created by the PC 43, but the report may be created in the endoscope apparatus 1. In such a case, the report creation processing program 45a and the template information are stored in the ROM 22, the memory card 11 or the like of the endoscope apparatus 1 which is the endoscope inspection report creation apparatus, the CPU 21 executes the program, and the report is created.

Furthermore, the entire or part of the program code of the software that executes the operation described above is recorded or stored in movable media such as a flexible disk and a CD-ROM, a storage device such as a hard disk, and the like, as computer program product. The program code is read by the computer, and the entire or part of the operation is executed. Alternatively, the entire or part of the program can be distributed or provided via a communication network. A user can easily realize the endoscope inspection report creating apparatus and method of the present invention by downloading the program via the communication network and installing the program in a computer, or installing the program in the computer from the storage medium.

The present invention is not limited to the aforementioned embodiment, and various modifications, alterations and the like can be made within the range without changing the gist of the present invention.

What is claimed is:

1. An endoscope inspection report creating apparatus, said apparatus comprising:
a device configured to store a plurality of endoscopic images included in a plurality of folders divided according to inspection information relating to one or more of: inspection target information, inspection location information, and inspection purpose information;
a file name reading section that reads a file name of an endoscopic image, wherein the file name of the endoscopic image includes inspection result information;
a report creating section that creates a predetermined report based on the file name read by the file name reading section and the endoscopic image corresponding to the read file name, wherein the report creating section creates the predetermined report by writing, in the predetermined report, the inspection result information that is included in the read file name and the endoscopic image corresponding to the read file name, in association with each other at a first position and a second position, respectively; and
a device configured to output the predetermined report to the user,
wherein the plurality of folders is constructed in a hierarchy and the file name includes one or more folder names to which the file name belongs.

2. The endoscope inspection report creating apparatus according to claim 1, wherein the file name further includes inspection purpose information, and
wherein the report creating section creates the predetermined report by writing in the predetermined report, in addition to the inspection result information at the first position and the endoscopic image at the second position, the inspection purpose information at a third position in association with the endoscopic image corresponding to the read file name.

3. The endoscope inspection report creating apparatus according to claim 1, wherein the inspection result information comprises information converted into predetermined inspection result inscription information.

4. The endoscope inspection report creating apparatus according to claim 2, wherein the inspection purpose information comprises information converted into predetermined inspection purpose inscription information.

5. The endoscope inspection report creating apparatus according to claim 2, wherein the file name further includes inspection location information, and
wherein the report creating section creates the predetermined report by writing in the predetermined report, in addition to the inspection result information at the first position and the endoscopic image at the second position, the inspection location information at a fourth position in association with the endoscopic image corresponding to the read file name.

6. The endoscope inspection report creating apparatus according to claim 2, further comprising a file presence/absence determining section that detects presence or absence of a file with respect to each of the plurality of folders,
wherein when the file presence/absence determining section detects absence of the file with respect to a folder, the report creating section writes, in the predetermined report, file absence information corresponding to the folder with respect to which the absence of the file is detected.

7. The endoscope inspection report creating apparatus according to claim 2, wherein the report creating section creates the predetermined report based on a template of the predetermined report.

8. The endoscope inspection report creating apparatus according to claim 7, wherein the template specifies the first, second, and third predetermined positions for the inspection result information, the endoscopic image, and the inspection purpose information, respectively, in the predetermined report.

9. The endoscope inspection report creating apparatus according to claim 8,
wherein the file name further includes inspection target information which indicates an inspection target, and which is separated from the inspection purpose information and the inspection result information with use of a predetermined symbol or character, and
wherein the report creating section writes the inspection target information at a fifth position in the predetermined report.

10. The endoscope inspection report creating apparatus according to claim 1, further comprising a template storing section that stores a template for the predetermined report, wherein, in the template, a position of a first input column in which the inspection result information included in the file name is to be inputted, and a position of a second input column in which the endoscopic image corresponding to the file name is to be inputted, are specified in advance, and
wherein the report creating section creates the predetermined report by inputting the inspection result information included in the file name read by the file name reading section in the first input column of the template and inputting the endoscopic image corresponding to the read file name in the second input column of the template.

11. The endoscope inspection report creating apparatus according to claim 10, wherein the report creating section performs processing to reduce the endoscopic image to a predetermined size before inputting the endoscopic image in the second input column.

12. The endoscope inspection report creating apparatus of claim 1, wherein the inspection result information comprises a file mark added to classify images into one or more of: 'accept', 'reject', 'repair', and 're-inspect'.

13. An endoscope inspection report creating method, said method comprising:
storing a plurality of endoscopic images included in a plurality of folders divided according to inspection information relating to one or more of: inspection target information, inspection location information, and inspection purpose information;
reading a file name of an endoscopic image, wherein the file name of the endoscopic image includes inspection result information;
creating a predetermined report based on the read file name and the endoscopic image corresponding to the read file name, wherein the predetermined report is created by writing, in the predetermined report, the inspection result information that is included in the read file name and the endoscopic image corresponding to the read file name, in association with each other at a first position and a second position, respectively; and
outputting the predetermined report to the user,
wherein the plurality of folders is constructed in a hierarchy and the file name includes one or more folder names to which the file name belongs.

14. The endoscope inspection report creating method according to claim 13, wherein the file name further includes inspection purpose information, and
wherein the predetermined report is created by writing in the predetermined report, in addition to the inspection result information at the first position and the endoscopic image at the second position, the inspection purpose information at a third position in association with the endoscopic image corresponding to the read file name.

15. The endoscope inspection report creating method according to claim 13, wherein the inspection result information comprises information converted into predetermined inspection result inscription information.

16. The endoscope inspection report creating method according to claim 14, wherein the inspection purpose information comprises information converted into predetermined inspection purpose inscription information.

17. The endoscope inspection report creating method according to claim 14, wherein the file name further includes inspection location information, and
wherein the predetermined report is created by writing in the predetermined report, in addition to the inspection result information at the first position and the endoscopic image at the second position, the inspection location information at a fourth position in association with the endoscopic image corresponding to the read file name.

18. The endoscope inspection report creating method according to claim 14, further comprising detecting a presence or absence of a file with respect to each of the plurality of folders,
wherein when absence of the file with respect to a folder is detected, file absence information corresponding to the folder with respect to which the absence of the file is detected is written in the predetermined report.

19. The endoscope inspection report creating method according to claim 14, wherein the predetermined report is created based on a template of the predetermined report.

20. The endoscope inspection report creating method according to claim 19, wherein the template specifies the first, second, and third predetermined positions for the inspection result information, the endoscopic image, and the inspection purpose information, respectively, in the predetermined report.

21. The endoscope inspection report creating method according to claim 13, wherein in a template for the predetermined report, a position of a first input column in which the inspection result information included in the read file name is to be inputted, and a position of a second input column in which the endoscopic image corresponding to the read file name is to be inputted, are specified in advance, and
wherein the predetermined report is created by inputting the inspection result information included in the read file name in the first input column of the template and inputting the endoscopic image corresponding to the read file name in the second input column of the template.

22. The endoscope inspection report creating method according to claim 21, further comprising reducing the endoscopic image to a predetermined size before inputting the endoscopic image in the second input column.

23. The endoscope inspection report creating method of claim 13, wherein the inspection result information comprises a file mark added to classify images into one or more of: 'accept', 'reject', 'repair', and 're-inspect'.

24. A non-transitory computer-readable storage medium including having stored thereon a program for creating an endoscope inspection report, the program causing a computer to perform functions comprising:

storing a plurality of endoscopic images included in a plurality of folders divided according to inspection information relating to one or more of: inspection target information, inspection location information, and inspection purpose information;

reading a file name of an endoscopic image, wherein the file name of the endoscopic image includes inspection result information;

creating a predetermined report based on the read file name and the endoscopic image corresponding to the read file name, wherein the predetermined report is created by writing, in the predetermined report, the inspection result information that is included in the read file name and the endoscopic image corresponding to the read file name, in association with each other at a first position and a second position, respectively; and outputting the predetermined report to the user, wherein the plurality of folders is constructed in a hierarchy and the file name includes one or more folder names to which the file name belongs.

25. The non-transitory computer-readable storage medium of claim 24, wherein the inspection result information comprises a file mark added to classify images into one or more of: 'accept', 'reject', 'repair', and 're-inspect'.

* * * * *